(12) United States Patent
Kaveckis et al.

(10) Patent No.: US 10,368,937 B2
(45) Date of Patent: Aug. 6, 2019

(54) FLUID DELIVERY SYSTEM AND METHOD FOR TREATMENT

(71) Applicant: Holaira, Inc., Plymouth, MN (US)

(72) Inventors: Ryan Kaveckis, Minneapolis, MN (US); Edward S. Harshman, Kirkland, WA (US); Martin L. Mayse, Bellevue, WA (US); John Streeter, Redmond, WA (US); Kyle True, Plymouth, MN (US); Richard C. Gunderson, Plymouth, MN (US)

(73) Assignee: Nuvaira, Inc., Plymouth, MN (US)

( * ) Notice: Subject to any disclaimer, the term of this patent is extended or adjusted under 35 U.S.C. 154(b) by 642 days.

(21) Appl. No.: 14/775,185

(22) PCT Filed: Mar. 13, 2014

(86) PCT No.: PCT/US2014/026547
§ 371 (c)(1),
(2) Date: Sep. 11, 2015

(87) PCT Pub. No.: WO2014/160422
PCT Pub. Date: Oct. 2, 2014

(65) Prior Publication Data
US 2016/0022351 A1   Jan. 28, 2016

Related U.S. Application Data

(60) Provisional application No. 61/779,371, filed on Mar. 13, 2013.

(51) Int. Cl.
*A61B 18/02* (2006.01)
*A61B 18/14* (2006.01)
*A61B 18/00* (2006.01)

(52) U.S. Cl.
CPC .......... *A61B 18/14* (2013.01); *A61B 18/1492* (2013.01); *A61B 2018/00023* (2013.01);
(Continued)

(58) Field of Classification Search
CPC ..... A61B 18/14; A61B 18/1492; A61B 18/02; A61B 2018/00005; A61B 2018/00011;
(Continued)

(56) References Cited

U.S. PATENT DOCUMENTS

| 4,919,134 A | 4/1990 | Streeter |
| 5,025,955 A | 6/1991 | Stenger |

(Continued)

FOREIGN PATENT DOCUMENTS

| CN | 102905639 A | 1/2013 |
| EP | 0175528 A1 | 3/1986 |

(Continued)

OTHER PUBLICATIONS

PCT/ISA/210 International Search Report for PCT/US2014/026547, dated Jul. 15, 2014, 11 pages.
(Continued)

*Primary Examiner* — Thomas A Giuliani
(74) *Attorney, Agent, or Firm* — Patterson Thuente Pedersen, P.A.

(57) ABSTRACT

A treatment system includes a fluid cooling supply system for chilling and delivering liquid coolant to a patient. The fluid cooling supply system includes a cooling device and a heat exchanger device. The heat exchanger device is biased to the cooling device and is in fluid communication with a treatment device in a patient. The fluid cooling supply system includes at least one biasing mechanism to provide a given biasing force between the heat exchanger device and the cooling device to effectuate and improve heat transfer. The liquid coolant may be circulated through an energy (Continued)

delivery device positioned in an airway of a patient to preserve tissue. The system is controlled to circulate liquid coolant at a given temperature and pressure for a selected amount of time during pulmonary treatment of a patient.

35 Claims, 28 Drawing Sheets

(52) U.S. Cl.
CPC ............... *A61B 2018/00029* (2013.01); *A61B 2018/00035* (2013.01); *A61B 2018/00434* (2013.01); *A61B 2018/00541* (2013.01); *A61B 2018/00577* (2013.01)

(58) Field of Classification Search
CPC .. A61B 2018/00023; A61B 2018/0212; A61B 2018/00541; A61B 2018/0243; A61B 2018/025; A61B 2018/0256
USPC .... 606/20–25, 41; 607/96, 98, 99, 104, 105, 607/113, 115, 116
See application file for complete search history.

(56) References Cited

U.S. PATENT DOCUMENTS

| | | | |
|---|---|---|---|
| 5,348,554 A | 9/1994 | Imran et al. | |
| 6,719,779 B2 | 4/2004 | Daoud | |
| 7,212,409 B1 | 5/2007 | Belady et al. | |
| 7,608,825 B2 | 10/2009 | Rajaraman et al. | |
| 7,975,491 B2* | 7/2011 | Smisson, III | A61M 5/44 165/185 |
| 8,088,127 B2 | 1/2012 | Mayse et al. | |
| 8,133,497 B2 | 3/2012 | Deem et al. | |
| 8,172,827 B2 | 5/2012 | Deem et al. | |
| 8,226,638 B2 | 7/2012 | Mayse et al. | |
| 8,338,164 B2 | 12/2012 | Deem et al. | |
| 8,483,831 B1 | 7/2013 | Hlavka et al. | |
| 8,489,192 B1 | 7/2013 | Hlavka et al. | |
| 2004/0226556 A1 | 11/2004 | Deem et al. | |
| 2004/0267340 A1* | 12/2004 | Cioanta | A61F 7/123 607/105 |
| 2006/0225742 A1 | 10/2006 | Deem et al. | |
| 2008/0146995 A1 | 6/2008 | Smisson et al. | |
| 2009/0125014 A1 | 5/2009 | Bouthillier et al. | |
| 2010/0094089 A1 | 4/2010 | Litscher et al. | |
| 2010/0280454 A1* | 11/2010 | Rosiello | A61M 5/44 604/114 |
| 2011/0118725 A1 | 5/2011 | Mayse et al. | |
| 2011/0152855 A1 | 6/2011 | Mayse et al. | |
| 2011/0257647 A1 | 10/2011 | Mayse et al. | |
| 2011/0301587 A1* | 12/2011 | Deem | A61B 18/1815 606/33 |
| 2012/0016363 A1 | 1/2012 | Mayse et al. | |
| 2012/0016364 A1 | 1/2012 | Mayse et al. | |
| 2012/0095536 A1 | 4/2012 | Machold et al. | |
| 2012/0203216 A1 | 8/2012 | Mayse et al. | |
| 2012/0203222 A1 | 8/2012 | Mayse et al. | |
| 2012/0209261 A1 | 8/2012 | Mayse et al. | |
| 2012/0209296 A1 | 8/2012 | Mayse et al. | |
| 2012/0283562 A1* | 11/2012 | Ginsburg | A61F 7/12 600/435 |
| 2012/0302909 A1 | 11/2012 | Mayse et al. | |
| 2012/0310233 A1 | 12/2012 | Dimmer et al. | |
| 2012/0316552 A1 | 12/2012 | Mayse et al. | |
| 2012/0316559 A1 | 12/2012 | Mayse et al. | |
| 2013/0123751 A1 | 5/2013 | Deem et al. | |
| 2013/0289555 A1 | 10/2013 | Mayse et al. | |
| 2013/0289556 A1 | 10/2013 | Mayse et al. | |
| 2013/0296647 A1 | 11/2013 | Mayse et al. | |
| 2013/0303948 A1 | 11/2013 | Deem et al. | |
| 2013/0310822 A1 | 11/2013 | Mayse et al. | |
| 2013/0345700 A1 | 12/2013 | Hlavka et al. | |
| 2014/0276792 A1* | 9/2014 | Kaveckis | A61B 18/1492 606/41 |
| 2016/0022351 A1 | 1/2016 | Kaveckis et al. | |

FOREIGN PATENT DOCUMENTS

| | | | |
|---|---|---|---|
| JP | 61-96938 | 6/1986 | |
| JP | 2009-136380 | * 6/2009 | ............... A61F 7/12 |
| JP | 2013508121 A | 3/2013 | |
| WO | WO 2008/047154 A2 | 4/2008 | |
| WO | WO 2011/12716 A2 | 10/2011 | |

OTHER PUBLICATIONS

PCT/ISA/237 Written Opinion for PCT/US2014/026547, dated Jul. 15, 2014, 23 pages.
Search Report dated Nov. 14, 2016 for EP Application No. 14773257.6, 7 pages.
Search Report dated Apr. 10, 2017 for EP Application No. 14773257.6, 11 pages.
Office Action dated Jan. 17, 2018 for Japanese Application No. 2016-502173, 14 pages.
Office Action dated Jan. 26, 2018 for Chinese Application No. 201480024398.0, 18 pages.
Office Action dated Sep. 11, 2018 for Japanese Application No. 2016502173, 16 pages.
Office Action dated Oct. 18, 2018 for Chinese Application No. 201480024398.0, 9 pages.
Application and File history for U.S. Appl. No. 14/209,940, filed Mar. 13, 2014. Inventors: Kaveckis et al.
Search Report dated Apr. 10, 2017 for EP Application No. 14773257.2, 11 pages.
Search Report dated Nov. 14, 2016 for EP Application No. 14773257.2, 7 pages.

* cited by examiner

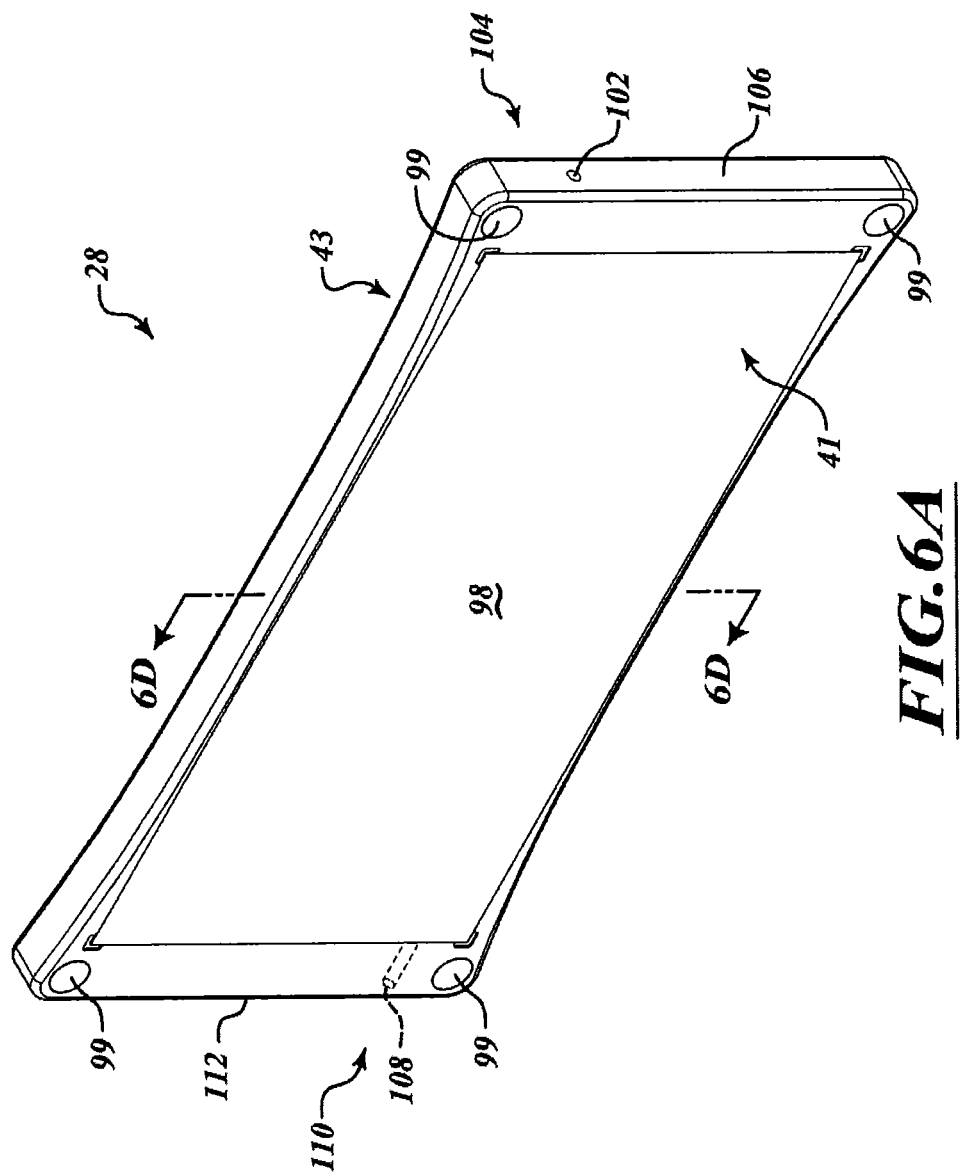

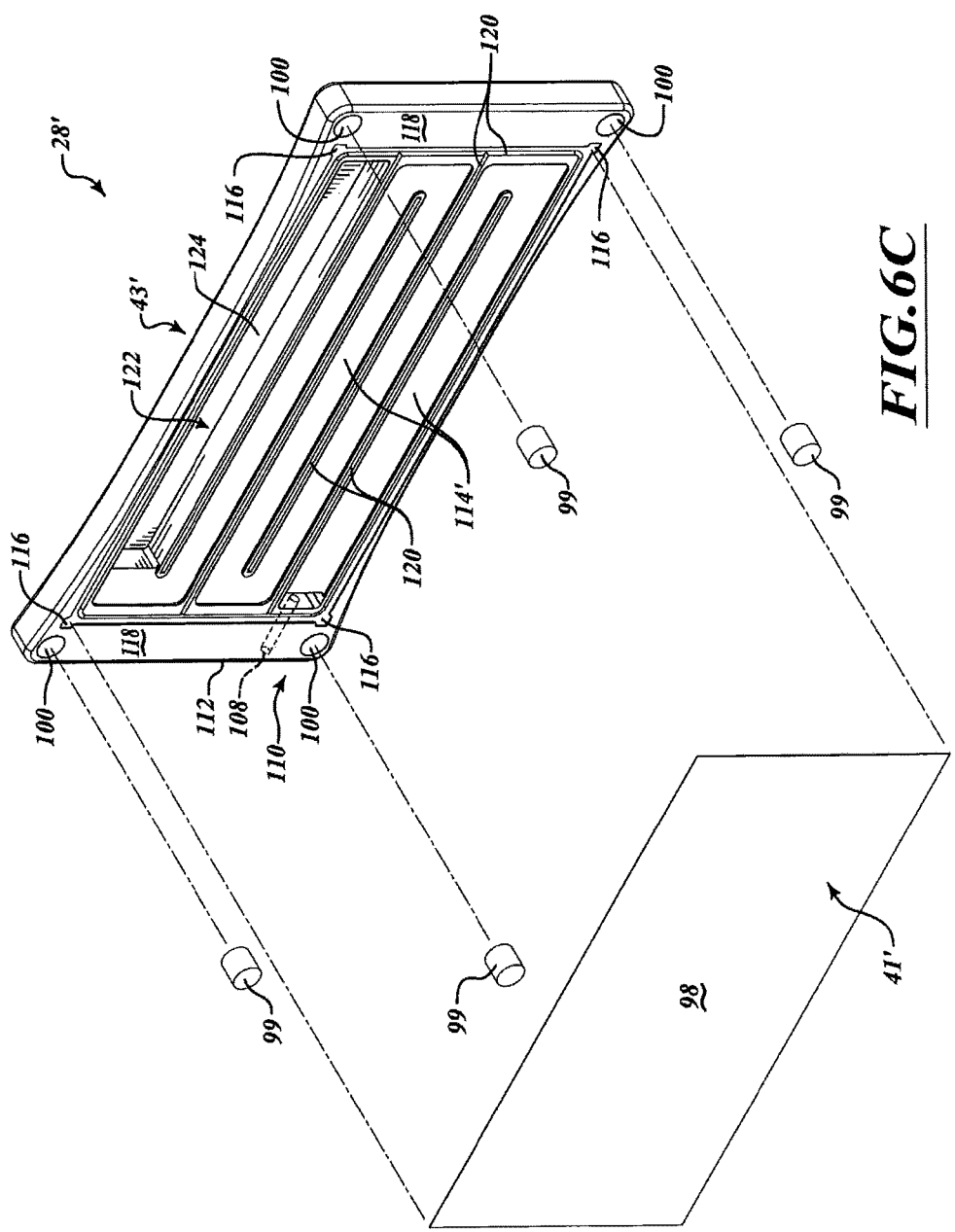

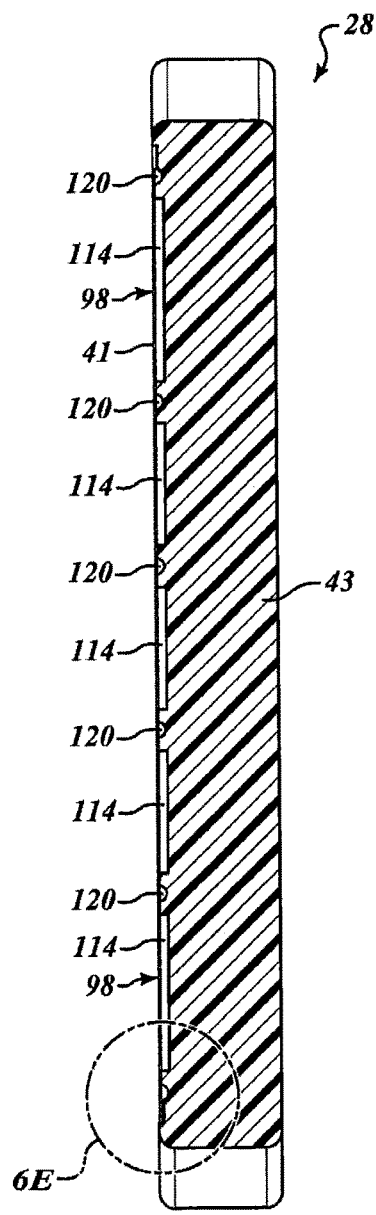
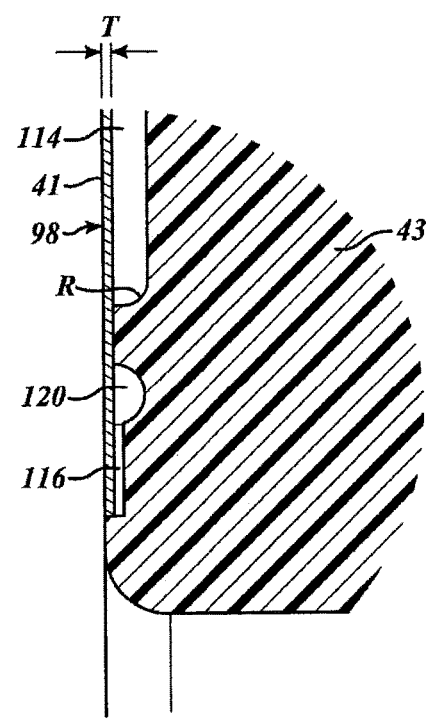
*FIG.6D*        *FIG.6E*

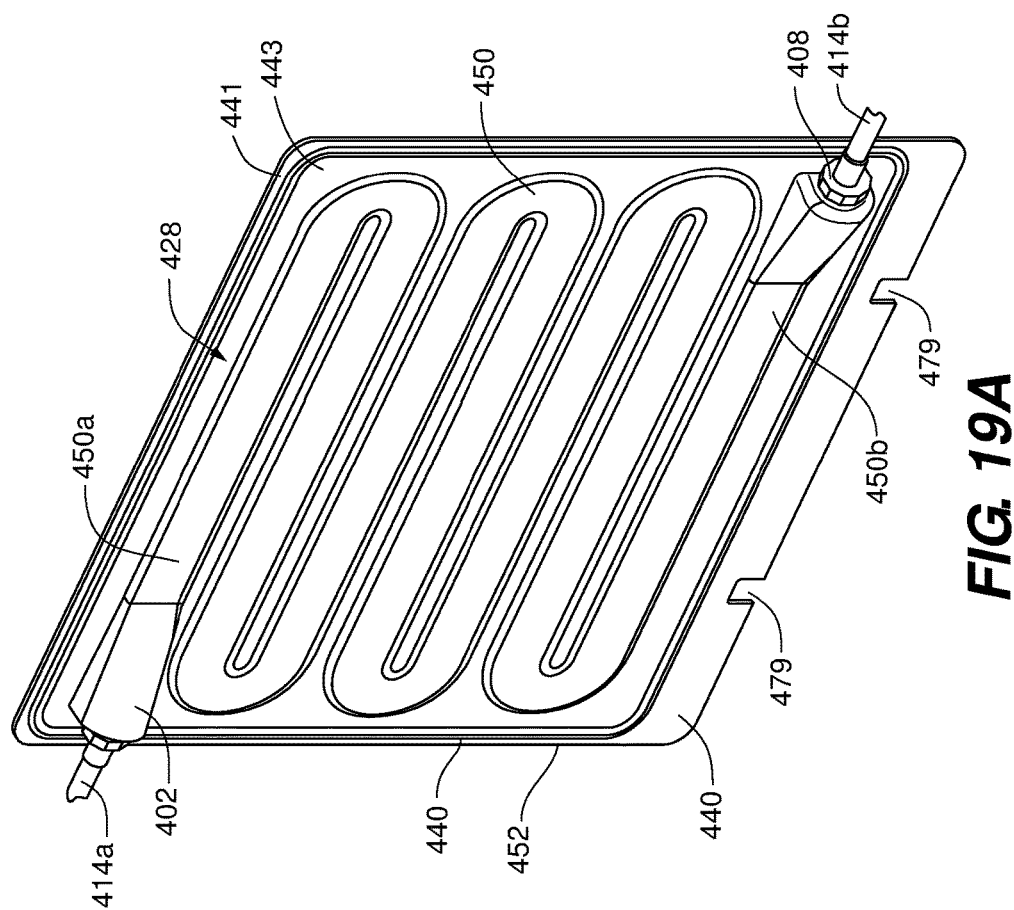

FLUID DELIVERY SYSTEM AND METHOD FOR TREATMENT

RELATED APPLICATION

The present application claims the benefit of U.S. Provisional Application No. 61/779,371 filed Mar. 13, 2013, which is incorporated herein in its entirety by reference.

TECHNICAL FIELD

The present invention generally relates to systems and associated methods for delivering a cooled fluid during treatment of a patient.

BACKGROUND

Description of the Related Art

Several conventional medical treatments include supplying a cooled liquid directly to the human body. For example, a cooled liquid may be supplied to the blood stream to cool an organ, such as the brain, to protect the organ from injury.

Other conventional medical treatments include supplying a cooled liquid to a device used to treat the human body. For example, several particularly effective treatments for pulmonary disorders are described in, for example, U.S. Pat. No. 8,088,127, titled, "Systems, Assemblies, and Methods for Treating a Bronchial Tree," and U.S. Patent Application Publication No. 2011/0152855, titled, "Delivery Devices With Coolable Energy Emitting Assemblies." In one example treatment described in these documents, a pulmonary treatment system delivers energy to damage a nerve trunk extending along an airway of a patient. In this example, the energy is delivered to a coolable energy emitter assembly and, simultaneously, chilled fluid is delivered to the energy emitter assembly to cool the energy emitter assembly to avoid or limit destruction of non-targeted tissue.

Conventional coolant supply systems typically include a pump which pumps a liquid coolant from a reservoir to the patient and/or treatment device. Depending on the type of therapy being performed, conventional liquid coolant supply systems can include relatively large reservoirs containing as much as five gallons of liquid coolant from which liquid coolant is supplied to the thermal therapy catheter. The liquid coolant contained within the large reservoir is, in many cases, simply maintained at room temperature. Other conventional liquid coolant supply systems have closed loop systems in which fluid is pumped from a reservoir and back to the reservoir after circulation through a device in a patient.

BRIEF SUMMARY

It has been recognized that delivering a liquid coolant to a treatment site in a patient during treatment can present several difficulties to practitioners. For example, it can be challenging to maintain a desired temperature (or range of temperatures) at a treatment site within a patient for a desired interval during a treatment session. This is partially due to heat losses that may exist from the time when the fluid is chilled to the time when the fluid is supplied to a patient for treating the tissue.

It has been recognized that conventional liquid coolant supply systems fail to provide a sufficiently compact and efficient closed loop system that allows for control of the temperature and pressure of a liquid coolant supplied to a treatment device positioned in a patient. In addition, conventional liquid coolant supply systems can be expensive and may, in some instances, require extensive and time consuming sterilization between treatments of different patients. Moreover, it has been recognized that conventional liquid coolant supply systems may not be ideal for use during certain treatments, such as the pulmonary treatment discussed above, because of requirements pertaining to size of an insertion device, temperature at a treatment site, duration of treatment, controllability of the system, and other requirements that may be specific to certain treatments of a patient.

According to one aspect of the present disclosure, a treatment system includes a fluid cooling supply system for treatment of a patient and is configured to chill a fluid and circulate the chilled fluid through a treatment device, such as an energy delivery device, positioned inside a patient. The fluid cooling supply system may include (or be coupled to) a fluid reservoir having a fluid or coolant contained therein. The fluid cooling supply system may include a cooling device having a thermal plate for thermally treating the fluid. A heat exchanger may be removably coupled to the cooling device with a given biasing force for effectuating heat transfer from the fluid contained in or traveling through the heat exchanger. The heat exchanger may be a replaceable or disposable heat exchanger cartridge that includes a thermally conductive surface and a fluid channel that extends through the cartridge. At least a portion of the fluid channel in the cartridge is arranged adjacent the thermally conductive surface. The fluid channel permits passage of the fluid during thermal treatment of the fluid by the cooling device. Accordingly, when the cartridge is coupled to the cooling device, the thermally conductive surface and the thermal plate are biased to each other such that operating the cooling device draws heat from fluid contained in the fluid channel of the cartridge; the chilled fluid may then be supplied to a patient for treatment.

In one aspect, the heat exchange cartridge is a flexible, and preferably disposable, thermoformed tray that is bonded to a plate having a thermally conductive surface. The flexible thermoformed tray includes a recessed serpentine structure defining a fluid channel when the tray is bonded to the plate. A first end of the channel includes an inlet port for coupling to an inlet supply line, and a second end of the channel includes an outlet port for coupling to an outlet supply line. A depth and width of the recessed serpentine structure is determined based on a desired residence time of fluid within the cartridge, the residence time being calculated based on the flow rate of the fluid, and the desired temperature change of the fluid from the inlet to the outlet of the cartridge.

In other aspects, the heat exchanger is a bag removably coupled to the cooling device with a given biasing force for effectuating heat transfer from fluid contained in or traveling through the bag. The bag may be removably coupled to the cooling device by a plate such that the bag is positioned between the cooling device and the plate, or the bag may be attached by other attachment devices. A common feature of effectuating proper heat transfer to achieve a desired fluid temperature is ensuring a given biasing force of the heat exchanger to the cooling device. Thus, the bag may be biased to the cooling device by a clamp, a plate having fasteners, or other such devices. The bag may include a fluid channel that extends through the bag and serpentines throughout. At least a portion of the bag is arranged adjacent the cooling device and is biased thereagainst such that operating the cooling device draws heat from fluid contained in the fluid channel of the bag; the chilled fluid may then be supplied to a patient for treatment.

The fluid cooling supply system may further include a pump to supply and/or circulate a volume of fluid to the patient. At least one controller may be coupled to the cooling device and the pump for regulating the amount heat transfer and fluid volume and pressure to supply to a patient. The fluid cooling supply system may also include a supply path and a return path, which may include a series of lines or tubes or fluid pathways. The supply path originates at the fluid reservoir where the fluid is traversed through a heat exchanger cartridge for chilling the fluid, and then traversed to a treatment device in a patient for cooling at a treatment site. The return path originates at the treatment device in the patient, and then the return path may traverse back to the fluid reservoir for continuous circulation of the fluid through the system. Thus, the fluid reservoir, the supply and return tubes, the fluid channel of the cartridge, and the treatment device are all in fluid communication with each other. Accordingly, the cooling device chills the fluid that the pump circulates throughout the system during treatment of the patient.

As can be appreciated in any aspect of the present disclosure, the fluid cooling supply system may be a closed loop system or an open loop system. In a closed loop system, the fluid is continuously supplied from and returned to the fluid reservoir for recirculation. In an open loop system, the fluid is supplied from the fluid reservoir to the treatment device and then discarded after circulation through the treatment device.

Regarding certain components of the fluid cooling supply system introduced above and according to some aspects, the fluid reservoir may be a bag or other device capable of holding a fluid. In a closed loop system, the fluid reservoir may be a collapsible bag (such as an IV bag used for holding and providing saline or other fluids) having a supply port for providing the fluid and a return port for receiving the fluid once circulated through the system. Using a collapsible bag can, advantageously, accommodate changes in fluid pressure resulting from pumping the fluid through the system from the fluid reservoir, whether pumped in a forward or reverse manner.

In some aspects the fluid reservoir may be fluidly connected to the closed loop system via a coaxial bag spike assembly. The coaxial double spike may include a hypotube inserted within and through a lumen of a female luer, thereby defining a coaxial arrangement of an inner channel and an outer channel. The assembly can further include a bag spike adapter with two ports for connecting the fluid supply and return lines with the inner and outer channels of the assembly. For example, the inner channel is in fluid communication with the return line and the outer channel is in fluid communication with a supply line. In an alternative embodiment, the outer channel is in fluid communication with the return line and the inner channel is in fluid communication with the supply line. Accordingly, the coaxial bag spike assembly precludes the need for a separate supply and return spike by allowing fluid to flow out of and into the fluid reservoir simultaneously. This also allows for standard commercially available IV bags to be utilized as coolant reservoirs.

The cooling device may be any appropriate cooling device, such as a thermoelectric cooler (hereinafter "TEC"), having a thermal plate for effective heat transfer from the fluid when a heat exchanger is coupled to the thermal plate. TECs are typically used for cooling applications and for controlling the amount of heat transfer from a material or fluid, as is well known in the art. TECs use the Peltier effect (or thermoelectric effect) to create a heat flux between the junction of two different types of materials. As such, a typical TEC includes a "hot plate" and a "cold plate" having a plurality of p-type and n-type semiconductors sandwiched between the plates. When a voltage is applied across the semiconductors, the TEC transfers heat from the cold plate to the hot plate, and the heat is dispersed from the hot plate by a heat sink and a fan, for example. Accordingly, the cooling device of the present disclosure is preferably a TEC having a thermal (cold) plate biased against a heat exchanger cartridge to remove heat from the fluid contained in the cartridge. It will be appreciated that other cooling devices or systems could be used to achieve the same result of cooling the fluid, such as refrigerator system or other cooling system coupled to or including a heat exchanger.

The pump is configured to supply and circulate chilled fluid through the treatment device. The pump may be further configured to regulate a volume and a pressure of fluid passing through the system. In some aspects the pump is a peristaltic pump that is coupled adjacent to the cooling device and the cartridge. A peristaltic pump has the capability to draw and push fluid through a tube without contacting the fluid to maintain sterility of the fluid. In a one example, the pump is positioned in a supply path between the heat exchanger cartridge and the patient (or downstream of the cartridge) such that the pump draws the fluid through the cartridge at a negative pressure and supplies chilled fluid to the treatment device at a positive pressure. Positioning the pump downstream of the cartridge in this manner provides several advantages. For example, the resulting negative pressure in the cartridge allows for greater flexibility in material and design choices of the cartridge. Smaller and thinner components can be used in the cartridge, resulting in greater heat transfer from the fluid during system operation. In some aspects, the positive pressure supplied to the energy delivery device is at least 80 psi, and the fluid is returned to the fluid reservoir and/or the cartridge from the treatment device at a pressure of 10 psi or less, although the pressure in the system may vary beyond such values depending upon system and patient requirements.

In some aspects, the pump is configured to circulate fluid through the system at a fluid flow rate of between 70 milliliters to 160 milliliters per minute, although the flow rate may vary beyond such range. Preferably, the flow rate is 100 milliliters per minute. In some aspects, the pump is configured to supply chilled fluid to the treatment device at a pressure between 25 psi and 150 psi, although the flow rate may vary beyond such range. Preferably, the pressure is between 80 psi and 100 psi.

In some aspects, the pump includes a forward gear and a reverse gear. The reverse gear is adapted to reverse the flow of the fluid through system to remove gas from the system before or during treatment of a patient. Removing gas or air bubbles from the system allows for an uninterrupted fluid supply during treatment and maximizes cooling of the fluid in the cartridge. The cartridge can also be positioned substantially vertical relative to horizontal and to include an inlet port positioned at an upper portion of the cartridge and an outlet port positioned at a lower portion of the cartridge. With this arrangement, reversing the pump direction will drive fluid back through the system, thereby removing gas from the fluid channel of the cartridge. In particular, the gas rises vertically through the cartridge, and eventually into a fluid reservoir for dissipation. The pump may then be engaged by its forward gear to supply chilled fluid during treatment of a patient. Even during forward, normal operation of the pump, gas that may exist in the cartridge may tend to rise upwardly due to the particular arrangement and configuration of the cartridge.

In some aspects, the fluid channel includes at least one corner portion proximate a transition between a first sidewall and a second side wall of the fluid channel. The at least one corner portion is configured such that gas bubbles are not trapped near or proximate the at least one corner portion during operation of the system. The corner portion may have a radius or chamfer at the transition between the first and second sidewalls of the channel. In addition, the fluid channel may have a cross sectional profile that has a rounded corner portion at upper and lower corners of the cross sectional profile. These features that reduce the cross sectional area of the fluid channel may assist to overcome the surface tension of gas bubbles that may otherwise become stuck in the corners due to the vertical orientation of the cartridge.

In one aspect, the heat exchanger cartridge includes a first plate and a second plate coupled to each other. The first plate includes a thermally conductive surface, which may be comprised of copper, aluminum, and/or stainless steel. The thermally conductive surface is preferably comprised of copper, and more preferably comprised of plated or anodized metals such as anodized aluminum or silver plated copper. The second plate includes a thermally insulating material, such a polymer or plastic, and includes a serpentine groove that defines at least a portion of the fluid channel. The serpentine groove may have a substantially flat profile relative to the thermal plate in order to maximize heat transfer from the fluid. The cartridge may include an input port coupled to a fluid reservoir that supplies fluid, and an output port coupled to the treatment device for supplying chilled fluid. As such, the input and output ports are in fluid communication with the fluid channel and the treatment device. In some aspects, the cartridge includes a variable volume reservoir contained in the cartridge such that fluid is drawn only from the variable volume reservoir and not from any other source. In such aspect, the fluid may then be discarded after circulation through the treatment device (open loop system), or the fluid may be returned to an inlet of the variable volume reservoir (closed loop system). In some aspects, a return fluid channel extends through a portion of the cartridge with at least a portion of the return fluid channel arranged adjacent to the thermally conductive surface such that the fluid in the return fluid channel is pre-cooled before returning to the fluid reservoir for recirculation.

In one aspect, the fluid cooling supply system may include at least one biasing mechanism to provide sufficient and given biasing force between the cartridge and the cooling device. The biasing mechanism can be at least one magnet arranged to removably couple the cartridge to the cooling device. The at least one magnet may be magnetically coupleable to at least one corresponding magnet adjacent the thermal plate of the cooling device, or it may be magnetically coupleable to a magnetically attractive element of the cooling device. The at least one biasing mechanism may include two pairs of magnets positioned on opposing ends of the cartridge and each coupleable to corresponding pairs of magnets adjacent the thermal plate. The corresponding pairs of magnets may be secured to a biasing frame coupled to the thermal plate of the cooling device. The biasing frame may extend around a perimeter of the thermal plate. The corresponding pairs of magnets of the biasing frame are aligned with and attractable to the pairs of magnets of the cartridge to bias the cartridge to the thermal plate with a given biasing force. The result of utilizing a naturally-occurring means and mechanism is that most or all of the surface area of the thermally conductive surface of the cartridge is biased against the most or all of the surface area of the thermal plate of the cooling device at a given biasing force to effectively and efficiently transfer heat from the fluid during cooling of the fluid.

In several aspects of the present disclosure the cooling system includes features that act to bias the cartridge to the cooling device with a sufficient and given force to effectuate and improve heat transfer from the fluid. Notably, available TECs are limited by the amount of heat flux that is able to be dissipated by the TEC; thus, desirable heat transfer of the fluid is somewhat limited in some applications. Also, TECs are known to be somewhat inefficient as compared to other cooling devices, so it is important to reduce efficiencies of the system in other aspects, such as the design of the cartridge and configuration of other components in the system, like the position of the pump. Furthermore, a sufficient biasing force between the thermally conductive surface of the cartridge and the thermal plate of the cooling device is important because of the nature of the material of the surfaces biased to each other. The thermally conductive surface may be copper and thermal plates are typically a ceramic substrate. Under a microscope, even the smoothest of cooper and ceramic surfaces show countless ridges and valleys that may affect thermal conductivity between the two materials if a sufficient biasing force is not applied and maintained during heat transfer. According, the present disclosure provides an effective means and various mechanisms to adequately bias the cartridge to the cooling device to increase surface-to-surface contact between the biased surfaces to efficiently chill the fluid during treatment of a patient. Such improved surface contact ultimately reduces heat losses in the system so that a constant and controllable fluid temperature is supplied to a treatment device in a patient. This is of particular importance when operating the cooling system during pulmonary treatment, which requires, at certain intervals, a constant fluid temperature and a constant fluid pressure for a particular duration during a treatment session.

In one aspect, the cartridge may be formed and provided in a pre-stressed configuration to improve heat transfer and reduce heat losses. Accordingly, the cartridge may be manufactured to be in a first state (pre-stressed) when disengaged from the cooling device, and in a second state when engaged to the cooling device. The first state is achieved by forming the cartridge to have a profile with a convex shape relative to the thermal plate of the cooling device such that a lateral arc of the cartridge extends from a left side to a right side of the cartridge. Accordingly, when the cartridge is engaged to the thermal plate (i.e., by utilizing the pairs of magnets on left and right sides of the cartridge, for example), by virtue of the convex shape and the force of the magnets, the thermally conductive surface of the cartridge will have a profile that is a substantially flat shape relative to the thermal plate because the magnets on the sides of the cartridge will tend to "flatten out" the profile of the cartridge. This pre-stressed configuration tends to prevent a slight "buckling" that may be experience by the cartridge such that the result would be a concave cartridge that is not completely or adequately biased to the cooling machine. Thus, the pre-stressed configuration of the cartridge provides greater surface-to-surface contact between the thermally conductive surface and the thermal plate, thereby resulting in improved heat transfer while reducing heat losses in the system. This is of particular importance when operating the cooling system during treatment of a patient because this particular pulmonary treatment requires, at certain intervals, a constant fluid temperature and a constant fluid pressure for a particular duration during a treatment session.

A method is provided for attaching and removing a heat exchanger cartridge from a cooling system for treatment of a patient. In some aspects, the method includes biasing a heat exchanger cartridge to a thermal plate of a cooling device, such as the cartridge and cooling device having the same or similar features discussed in the present disclosure. The method includes removing the heat exchanger cartridge from the cooling device, which may occur after treatment of one or more patients or treatment sessions. The method includes biasing a replacement heat exchanger cartridge to the thermal plate of the cooling device. The step of biasing the cartridges may include engaging magnets or other biasing mechanisms such that a given biasing force is applied to the cartridge to effectuate efficient heat transfer from the fluid. In preferred configurations, the given biasing force is at least 10 pounds of force, and is between 10 and 60 pounds of force, but the given biasing force may vary beyond such values and ranges. The given biasing force provided by the magnets permits biasing of the thermally conductive surface of the cartridges to the thermal plate of the cooling device. Because of the configuration of the magnets, biasing the cartridge to the cooling device occurs automatically such that the cartridge is positioned at approximately the same position on the cooling device with each replacement cartridge. This provides one advantage of a system that maintains consistency of position for every replaceable cartridge coupled to a cooling device, and therefore provides consistency of efficiency of chilling the fluid in the cartridge with repeated uses of system and replacement cartridges. The method may further include pumping the fluid through the heat exchanger cartridge for delivery to the patient before removing the heat exchanger cartridge from the cooling device. The method may further include supplying chilled fluid to a treatment device (e.g., energy delivery device) positioned adjacent to pulmonary tissue of the patient during a pulmonary treatment.

In another aspect, the fluid cooling supply system may include a cooling device with a thermal plate for cooling fluid, a disposable heat exchanger cartridge removably coupled to the thermal plate, and at least one biasing mechanism coupled to the cartridge and the cooling device to transfer heat from the fluid contained in the cartridge. The cartridge may include a first plate and a second plate coupled to each other wherein the first plate includes a thermally conductive surface, such as copper, aluminum, and/or stainless steel, and the second plate includes a thermally insulating material, such as polymer, ABS, nylon, or polycarbonate. The second plate may include a serpentine groove defining a fluid channel, similar to the cartridge discussed with reference to the magnetically attractable cartridge. In one configuration, the cartridge includes an upper angled surface and a corresponding lower angled surface to be received into a front plate for biasing to the cooling device. The cartridge may include a handle at an end of the cartridge for easy removal and replacement of the cartridge. A backside of the second plate may include a plurality of recesses for improved heat transfer of the fluid via the cooling device.

The cartridge may include a fluid reservoir for supplying fluid through the system; the fluid reservoir may be wholly contained in the cartridge or may be coupled to an outer portion of the cartridge. Accordingly, the second plate includes a fluid reservoir in fluid communication with the fluid channel and positioned at an upper portion of the cartridge. The fluid reservoir in this aspect may be a collapsible bag positioned in a cavity in the second plate. The fluid is supplied from the fluid reservoir to a treatment device and may be either returned to the fluid reservoir in a closed loop system, or discarded as waste in open loop system. Providing a fluid reservoir inside of the cartridge itself provides an advantage of reducing the number of components and steps to set up and operate the system, which ensures sterility of the fluid as it reduces risk of human error due to incorrect installation or use of unsterile components. It also provides an advantage that the fluid in the reservoir is cooled by cooling device during operation, as opposed to providing room temperature fluid from an external fluid reservoir.

The at least one biasing mechanism may be a cam system that has a first position for engaging the cartridge to the cooling device and a second position for disengaging the cartridge from the cooling device. As further discussed in the present disclosure, providing a biasing mechanism (such as this cam system) provides an effective means to adequately bias the thermally conductive surface of the cartridge against the thermal plate of the cooling device with a sufficient and given force in order to increase surface-to-surface contact between the cartridge and the cooling device. In some aspects, a front plate is coupled to the front of a housing containing the cooling device. The cam system, the front plate, and the cartridge operate together to bias the cartridge to the thermal plate. The front plate includes an opening to receive the thermal plate of the cooling device and to facilitate biasing of the cartridge to the thermal plate. The front plate may have a slot sized to slideably receive the cartridge. The slot of the front plate includes an upper biasing surface and a lower biasing surface. The upper and lower biasing surfaces are each non-parallel to the thermal plate and may correspond to the upper and lower angled surfaces of the cartridge. Thus, the slot may have a trapezoid-shaped cross sectional profile that corresponds to a trapezoid-shaped cross sectional profile of the cartridge. Accordingly, the cartridge may be slideably receivable in the slot of the front plate when the cam system is disengaged (or unlocked). Once the cartridge is positioned in the slot, the cam system may be engaged (or locked) to apply a given biasing force to the cartridge against the cooling device to effectuate cooling of the fluid during operation of the system.

In some configurations, the cam system includes a cam lever, a cam shaft having at least one cam lobe, an actuation member coupled to the cartridge, and at least one actuation device coupled to the actuation member and coupleable to the cam lobes. The cam lever is either directly attached to the cam shaft or dynamically linked to the cam shaft. In some configurations, four cam lobes are formed along a length of the cam shaft and spatially separated from each other, although the four cam lobes may be a single cam lobe or cam device. Corresponding to the position of the four cam lobes may be four actuation devices, coupled to the actuation member, and positioned adjacent respective cam lobes. The four actuation devices are actuated downwardly by the respective cam lobes when the cam shaft is rotated by movement of the cam lever from the disengaged state to the engaged state. The actuation member has a lower actuation surface that may be formed at an angle that may correspond to the angle of the upper angled surface of the cartridge. Thus, engaging the cam system will bias the lower actuation surface to the upper angled surface of the cartridge, which tends to force the cartridge slightly downwardly and inwardly toward the cooling device because of the trapezoid-shaped profiles of the slot and the cartridge and the angle of the lower actuation surface, which collectively tend to bias the cartridge against the cooling device in a lateral direction with a given biasing force when the cam system is engaged.

A method is provided to provide a replaceable heat exchanger cartridge to a cooling device utilizing a cam system. The method may include biasing the cartridge to the cooling device by actuating the cam system to an engaged state. The method may include actuating the cam system to a disengaged state to release the biasing force on the cartridge. The method may include removing the cartridge and replacing it with a replacement cartridge, which may be biased to the cooling device with the cam system during treatment of a patient.

In another aspect, the at least one biasing mechanism may be a hinged door hingedly coupled to the cooling device and biased towards a closed position, thereby sandwiching the cartridge between the hinged door and the cooling surface of the cooling device. In this embodiment, one or more magnets may be employed on opposing surfaces of the door and/or the cooling device to provide a sufficient force in order to increase surface-to-surface contact between the cartridge and the cooling device. In one aspect, the cartridge may be configured with one or more notches defined in at a least one side edge of the cartridge for alignment with one or more keys of the cooling device to ensure that the cartridge is inserted in an orientation that allows for normal operation.

According to some aspects of the present disclosure, a method of cooling fluid for treatment of a patient is provided. The method may include drawing a coolant through a heat exchanger at a negative pressure to chill the coolant. The method may further include positioning a treatment device inside a bronchus of the patient and supplying the coolant to the treatment device to transfer heat from the patient during treatment. The method may include supplying the coolant from a reservoir and returning the fluid to the reservoir in a closed loop system. Alternatively, the method may include supplying the coolant from a reservoir and disposing of the fluid after transferring heat from the patient to the fluid in an open loop system. The method may include supplying the fluid to the treatment device in a positive pressure. The method may include regulating the amount of heat transfer from the coolant with a controller coupled to a cooling device, and regulating the amount of volume of fluid to supply for treatment of the patient with a controller coupled to a pump.

According to some aspects of the present disclosure, a method of cooling fluid for treatment of a patient is provided. The method may include positioning a heat exchanger against a cooling device. The heat exchanger may comprise some or all of the features of the cartridges discussed in the present disclosure. The method may include positioning the heat exchanger in a substantially vertical orientation such that gas rises in the heat exchanger. The method may include positioning a pump at a downstream side of the heat exchanger and pumping the fluid through the heat exchanger in a reverse manner to substantially remove gas from the heat exchanger and a system. The method may further comprise some or all of the steps for providing cooled fluid to a patient as discussed in the present disclosure.

In some aspects according to the present disclosure, a system for treatment of a patient is provided. The system may include a fluid cooling supply device configured to draw a fluid through a heat exchanger at a negative pressure to chill the fluid and to deliver the chilled fluid to the patient at a positive pressure. The fluid cooling supply device may include some or all of the features discussed in the present disclosure, such as the cooling device, pump, controller, housing, and front plate. Likewise, the heat exchanger may include some or all of the features of the cartridges discussed in the present disclosure. The system may include an energy delivery device positioned in the patient and coupled to the fluid cooling supply device such that the fluid cooling supply device circulates the chilled fluid through the energy delivery device to cool the energy delivery device during treatment of the patient. The energy deliver device may include an electrode adapted to deliver energy to a target tissue of the patient. The energy deliver device may include a cooling member arranged adjacent the electrode. The cooling member may be configured to allow circulation of the fluid from the fluid cooling supply device. The electrode and the cooling member are arranged adjacent to a wall of an airway of the patient such that the delivery of energy to the electrode and circulation of chilled fluid through the cooling member damages nerve tissue so that nervous system signals in the patient are attenuated while preserving tissue. The system may include a pump downstream from the cooling device and configured to circulate the fluid to through the energy delivery device at the positive pressure. The method may further comprise some or all of the steps for providing cooled fluid to a patient discussed in the present disclosure.

In some aspects of the present disclosure, the temperature of the fluid supplied by the fluid cooling supply system (or by any other system and method described in the present disclosure) may be provided at a given temperature or range at the location of the energy delivery device or other treatment device. It is preferred that the temperature at the energy delivery device energy is maintained at or below 20° C. during treatment of the patient. In a preferred configuration, the temperature at the energy delivery device is maintained between 20° C. and −5° C. during treatment of the patient. In an even more preferred configuration, the temperature at the energy delivery device is maintained between 5° C. and −2° C. during treatment of the patient. The temperature may vary beyond such ranges, however, depending upon system and patient requirements. In some aspects, a fluid is supplied to a patient at a given temperature for a selected amount of time during a treatment portion of treatment of the patient, or during an entire treatment process of the patient. In some configurations, the selected amount of time for a particular treatment portion is up to 120 seconds to provide the fluid having a given temperature. In some configurations, the selected amount of time for a particular treatment portion is less than 60 seconds. In some configurations, the selected amount of time for a particular treatment portion is between 60 and 120 seconds to provide the fluid having a given temperature. In some configurations, the selected amount of time for a particular treatment portion at least 120 seconds to provide the fluid having a given temperature. The selected amount of time may vary beyond such values and ranges, however, depending upon system and patient requirements. In some configurations, the fluid contained in the heat exchanger cartridge may be cooled to a temperature of at least 20° C., upon exiting the cartridge, and more preferable the fluid is cooled to a temperature between 5° C. and −5° C. upon exiting the cartridge, although the temperature of the fluid in the cartridge may vary beyond such values and ranges.

In some aspects, a method of treating a patient is provided. The method may include providing a cooling device having a fluid heat exchanger to deliver fluid to the patient, such as the cooling devices and heat exchanger cartridges discussed in the present disclosure. The method may include positioning an ablation assembly of a delivery device within an airway of the patient such that the ablation assembly is apposed against a wall of the airway. The ablation assembly may include an electrode adapted to deliver energy. The method may include coupling a fluid heat exchanger to the ablation assembly to be in fluid communication with each other. The method may include chilling the fluid in the fluid heat exchanger with a cooling device and treating tissue by circulating the fluid from the fluid heat exchanger through the delivery device. The method may include, simultaneously, delivering energy from the electrode of the ablation assembly to treat tissue adjacent the airway of the patient. As such, the method may include damaging nerve tissue of a nerve trunk adjacent the airway such that nervous system signals transmitted to a portion of the bronchial tree are attenuated. As discussed in the present disclosure, the fluid may be drawn through the fluid heat exchanger at a negative pressure and supplied to the delivery device at a positive pressure. During treatment, the fluid in the heat exchanger is cooled by the cooling device at a given temperature, and the fluid is supplied to (or circulated through) the delivery device at a given temperature and for a selected amount of time, as further discussed in the present disclosure.

As will be appreciated by a person having ordinary skill in the art reviewing this disclosure in detail, the methods and systems pertaining to the fluid cooling supply systems and heat exchanger cartridges can be combined in various aspects while still achieving the result of circulating chilled fluid through a treatment device positioned in a patient during treatment of the patient, as further discussed herein.

BRIEF DESCRIPTION OF THE SEVERAL VIEWS OF THE DRAWINGS

FIG. 6A is an isometric view of a heat exchanger cartridge according to one aspect.

FIG. 6C is an exploded view of a heat exchanger according to one aspect.

FIG. 6D is cross sectional side view of the heat exchanger of FIG. 6A, taken along lines 6D-6D of FIG. 6A.

FIG. 6E is a cutout view of a portion of the heat exchanger of FIG. 6D.

FIG. 19A is a front perspective view of a heat exchanger cartridge according to one aspect.

DETAILED DESCRIPTION

According to the present disclosure, FIGS. 1-7B illustrate a first aspect of a treatment system having a fluid cooling supply system for treatment of a patient, FIGS. 8-13C illustrate a second aspect of a treatment system having a fluid cooling supply system for treatment of a patient, and FIGS. 14-20 illustrate a third aspect of a treatment system having a fluid cooling supply system for treatment of a patient. It will be understood that various configurations described with reference to the first and second aspects may be combined into further configurations and aspects, which may be further discussed in the present disclosure regarding particular configurations.

Figure 1:
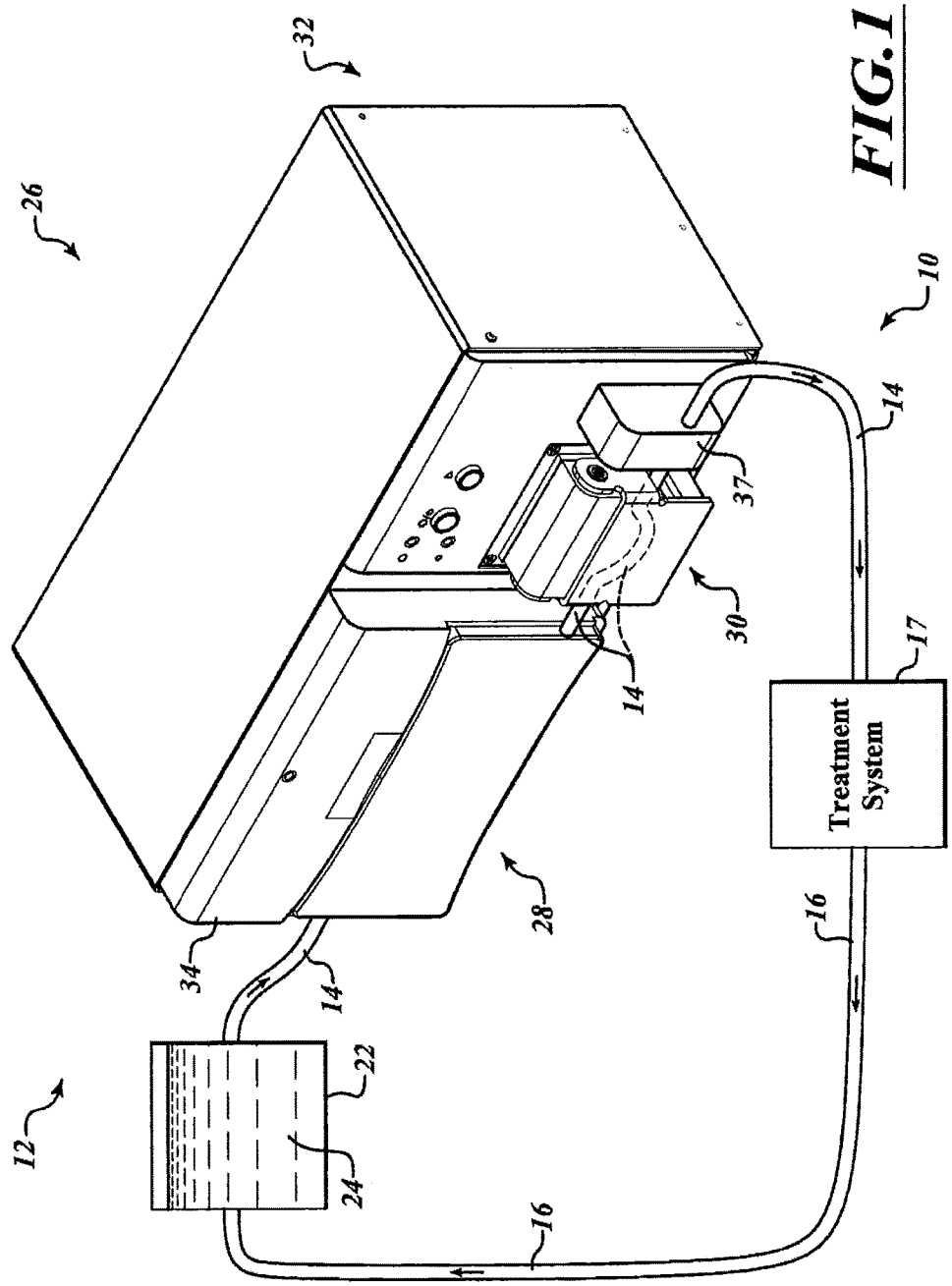
FIG. 1 is a perspective view of a treatment system having a fluid cooling delivery system according to one aspect.
Figure 2:
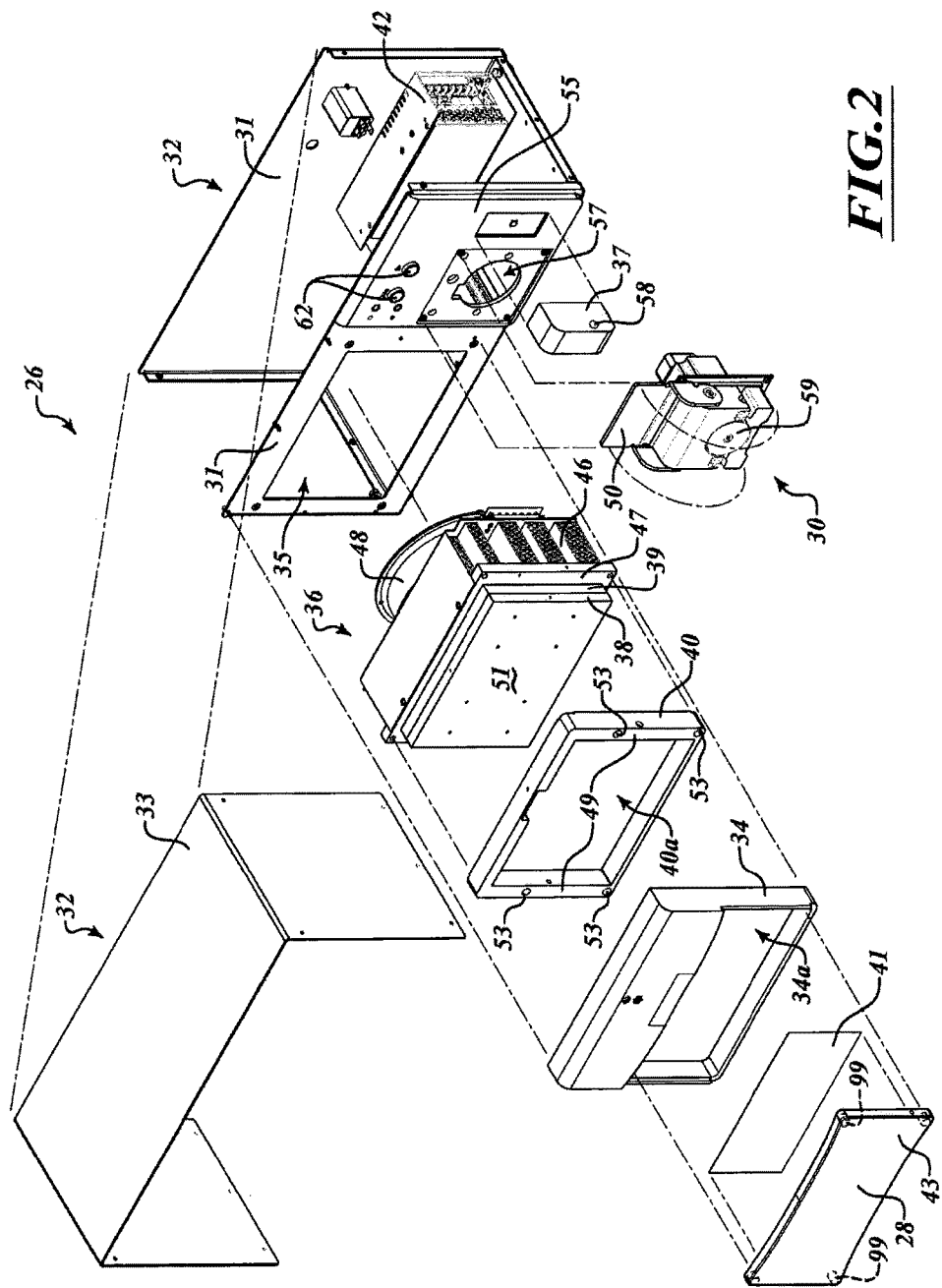
FIG. 2 is a partially exploded view of a fluid cooling delivery system according to one aspect.

FIGS. 1 and 2 illustrate a system 10 that includes a fluid cooling supply system 12 coupled to a treatment system 17. FIG. 2 shows a partially exploded view of certain components of the fluid cooling supply system 12 of FIG. 1.

Figure 4:
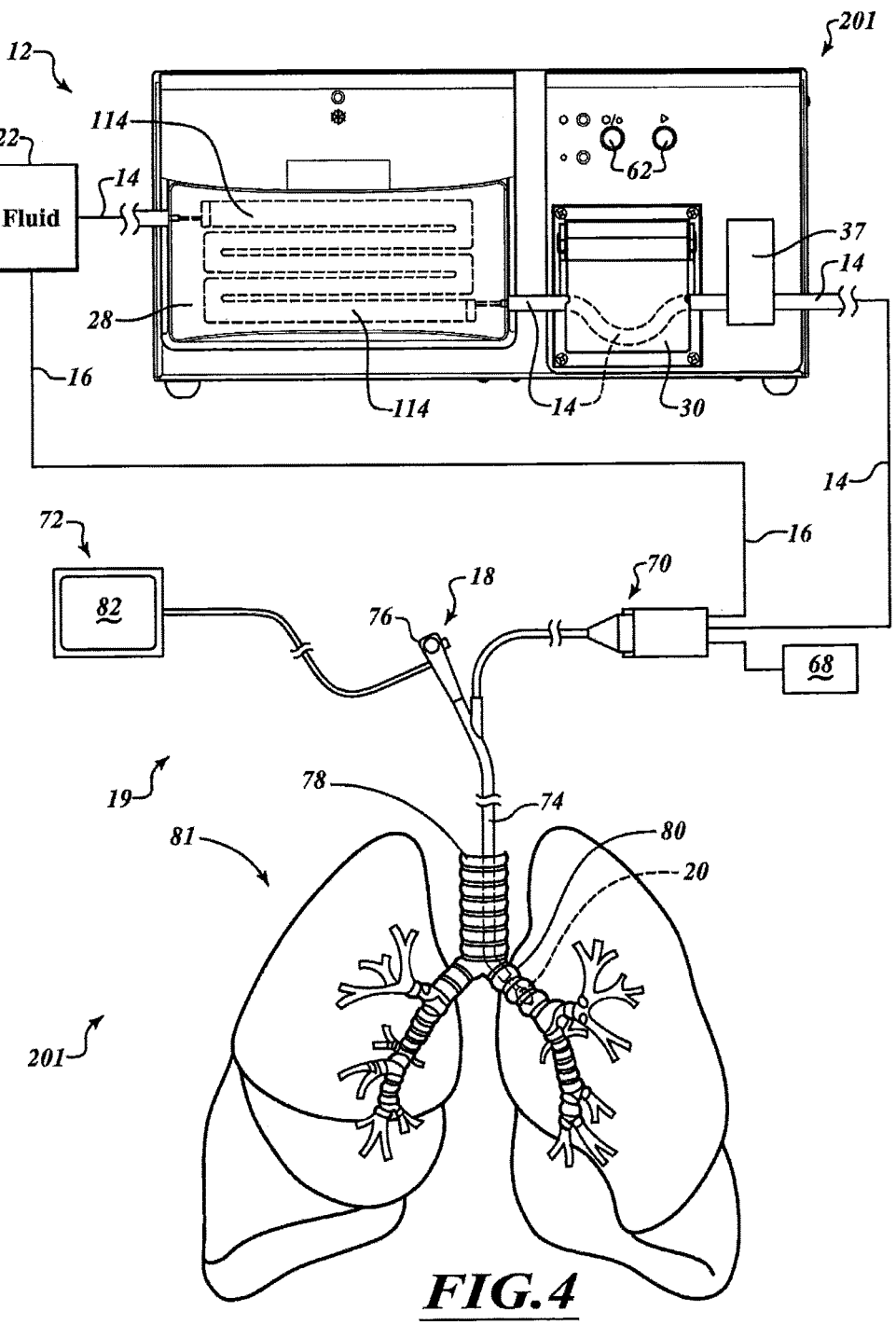
FIG. 4 is a front view of a fluid cooling delivery system and a schematic illustration of a treatment system during a treatment session according to one aspect.

In the example in FIG. 1, the fluid cooling supply system 12 is coupled to the treatment system 17. The treatment system 17 may be positionable at least partially in a patient (FIG. 4). The fluid cooling supply system 12 is configured to chill a fluid, pump the fluid, and supply the fluid through the treatment system 17. In a closed loop system, the fluid cooling supply system 12 may include a fluid reservoir 22, a fluid 24, a cooling system 26, a heat exchanger cartridge 28, and a supply line 14 and a return line 16, which collectively cooperate to circulate cooled fluid through the treatment system 17 during treatment. The supply line 14 originates at the fluid reservoir 22 and extends through the cartridge 28 and along a pump 30. The supply line 14 may extend through a pulse damper 37 for damping vibration of the supply line 14 during operation of the pump 30. Finally, the supply line 14 extends into the treatment system 17 positionable in a patient. The return line 16, in fluid communication with the supply line 14, originates at the treatment system 17 and extends from inside the patient and back to the reservoir 22 for recirculation of the fluid during treatment.

FIG. 2 further shows an exploded view of portions of the cooling system 26. The cooling system 26 may include a housing 32, a cooling device 36, a heat exchanger cartridge 28, a controller 42, and a pump 30. The housing 32 includes a first portion 31, a second portion 33 and a front plate 34 coupled to the first portion 31. The first portion 31 and second portion 33 of the housing 32 are removably attached to each other and are configured to structurally support and house various components of the system. The cooling device 36 has a thermal plate 38 extending at least partially through the front plate 34. The front plate 34 is secured to a front area of the first portion 31 of the housing 32. The front plate 34 and the housing 32 cooperate to structurally support the cooling device 36 and to position the thermal plate 38 substantially vertical. The front plate 34 includes an opening 34a for receiving the thermal plate 38 of the cooling device 36 and for facilitating biasing of the cartridge 28 to the thermal plate 38 (FIG. 7B). The housing 32 further includes a spacer 40 positioned between the cooling device 36 and the front plate 34 for additional support of the cooling device 36 and to allow egress of the thermal plate 38 through the front plate 34.

The cooling device 36 may be, for example, a conventional TEC that includes the thermal plate 38, a hot plate 39, fins 46, and a fan 48. The front portion 31 of the housing includes an opening 35 for receiving the cooling device 36 such that the thermal plate 38 extends out of the housing 32. A support plate 47 of the cooling device 36 may be secured to the first portion 31 of the housing 32 to properly position the cooling device 36. The support plate 47 may further be secured to the spacer 40 and front plate 34 for additional structural support.

The spacer 40 is coupled between the front plate 34 and the cooling device 36. The spacer 40 includes an opening 40a to allow egress of the thermal plate 38 and to position the thermal plate 38 adjacent the opening 34a of the front plate 34. The spacer 40 extends around a perimeter of the thermal plate 38 and the hot plate 39. Accordingly, an outer surface 49 of the spacer 40 and a planar surface 51 of the thermal plate 38 are substantially planar to each other (FIG. 7B) so that the cartridge 28 may be biased to the thermal plate 38.

Figure 6B:
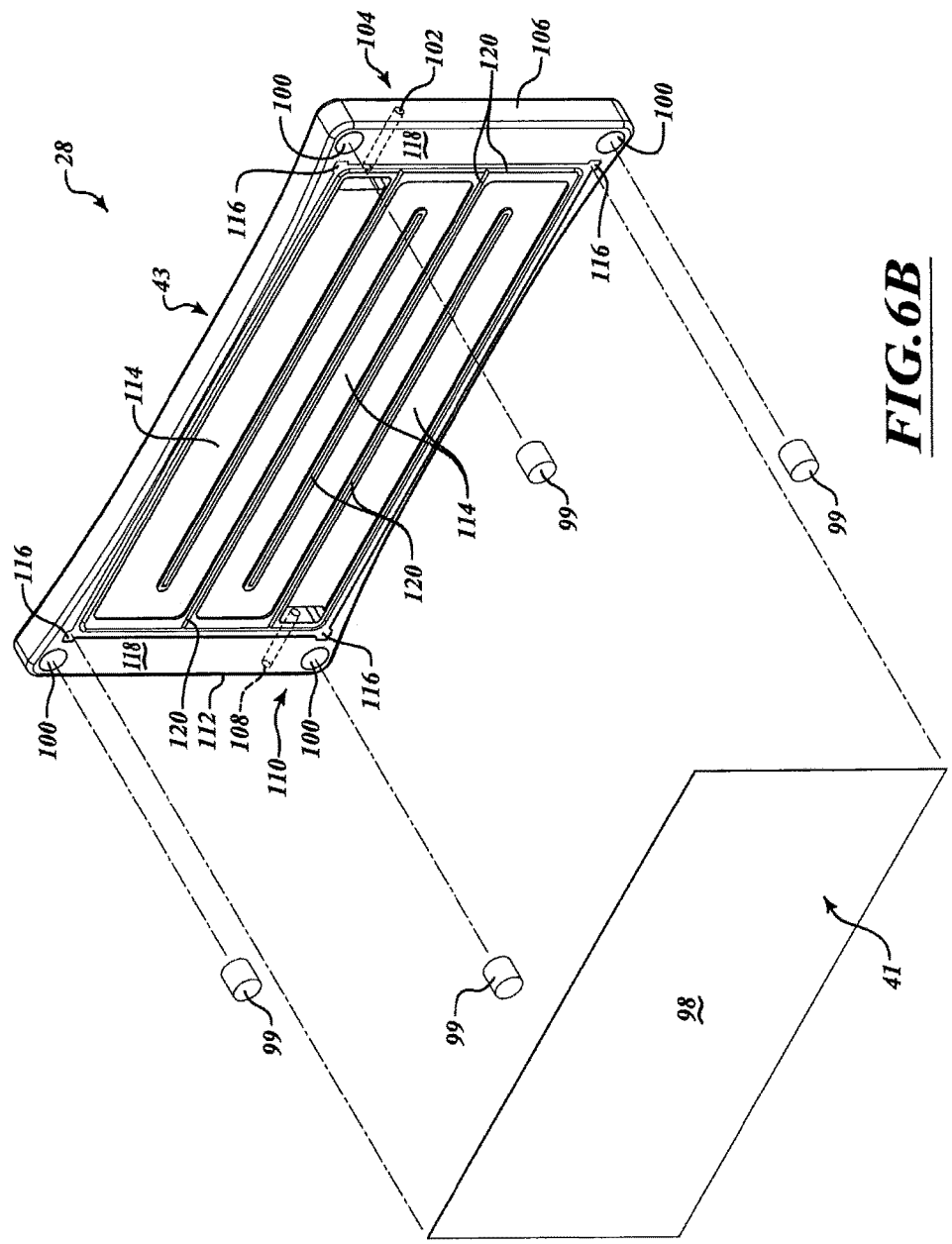
FIG. 6B is an exploded view of a heat exchanger according to one aspect.

The heat exchanger cartridge 28 includes a first plate 41 and a second plate 43. Magnets 99 are positioned in the second plate 43 (FIG. 6A). The spacer 40 includes four magnets 53 positioned at corresponding positions to engage the magnets 99 of the heat exchanger cartridge 28. Thus, the magnets 99 of the second plate 43 are magnetically coupled to the magnets 53 in the spacer 40 to removably couple the cartridge 28 to the thermal plate 38. Thus, the first plate 41 is biased to the planar surface 51 of the thermal plate 38 with a given biasing force to effectuate heat transfer of fluid contained in the cartridge 28 (FIGS. 6A-6C and 7B).

A controller plate 55 may be secured to a front area of the first portion 31 of the housing 32. The controller plate 55 may include an opening 57 for receiving the pump 30. The pump 30 may be a peristaltic pump having a cover 50 and a rotating device 59 for coupling to the supply line 14, such as with available peristaltic pumps. The fluid supply tube is placed in the pump in contact with the rotating device. The cammed surfaces on the rotating device cause periodic pressurization of the fluid in the fluid supply line. The pump 30 can include clamping mechanisms on the upstream and downstream sides thereof to ensure that the fluid supply line does not get pulled into the rotating device when the pump direction is reversed. In the present example, the pump 30 is positioned downstream of the cartridge 28 such that the cartridge 28 experiences a negative fluid pressure and the treatment system 17 experiences a positive fluid pressure during normal operation of the treatment system.

A pulse damper 37 may be removably attached to the controller plate 55. The damper 37 can be, for example, a chamber that includes an inlet and an outlet. The chamber accumulates a volume of fluid immediately downstream of the pump. The damper acts in a manner similar to a capacitor in a signal filtering device in that it smoothes the pressure oscillations generated by the rotating device of the pump.

Figure 3:
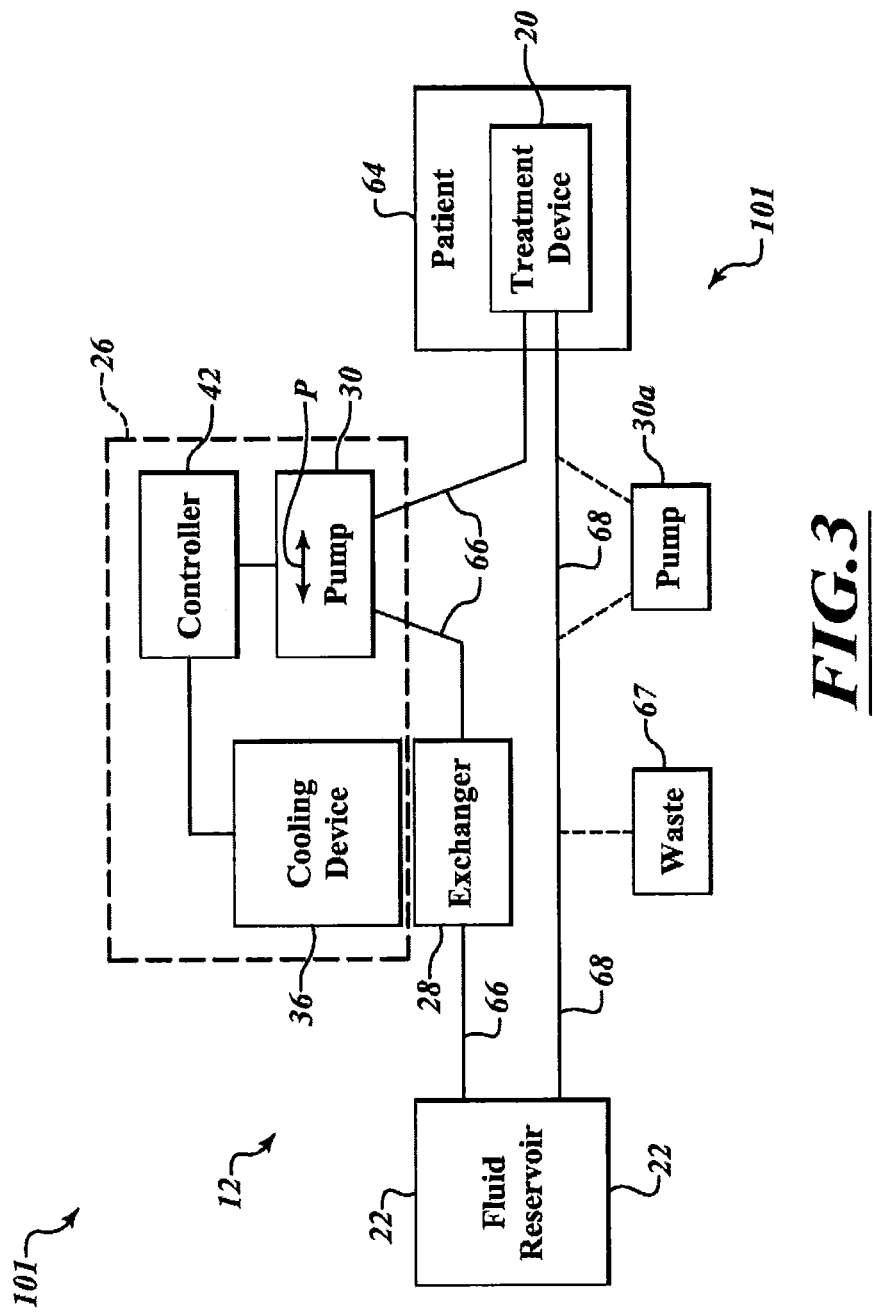
FIG. 3 is a schematic illustration of a fluid cooling delivery system coupled to a patient.

A controller system 60 includes control devices 62 and the controller 42 for controlling fluid temperature, pressure, and velocity. The control devices 62 are provided on the controller plate 55 and are coupled to the controller 42. A practitioner may operate the control devices 62 to control the system. The controller 42 may be operably coupled to the pump 30 to regulate the speed and direction of the pump 30, thereby regulating the direction of flow and amount of volume of fluid circulating through the system (FIG. 3). The controller 42 may also be operably coupled to the cooling device 36 for regulating the temperature of the fluid in the cartridge 28, thereby regulating the temperature of the fluid circulating through the treatment system 17, and thereby further regulating the temperature of a treatment device and/or patient tissue (FIG. 4). Performance can be optimized based on feedback from sensors that detect fluid and tissue temperatures, tissue impedance, and fluid supply to the treatment device (e.g., a pressure sensor, a temperature sensor, a thermocouple, a contact sensor, or the like). Accordingly, if surface temperature of patient tissue becomes excessively hot, fluid cooling can be increased by the cooling device 36 and/or electrode power can be decreased in order to produce deep lesions while protecting surface tissues.

FIG. 3 is a schematic illustration of a treatment system 101 according to one aspect of the present disclosure. The treatment system 101 includes a fluid cooling supply system 12 having a cooling system 26, a heat exchanger 28, and a fluid reservoir 22. The fluid cooling supply system 12 includes a cooling device 36, a controller 42, and a pump 30. The heat exchanger 28 is coupled to the fluid reservoir 22, the cooling device 36, and the pump 30. A supply path 66 and a return path 68 extend from the fluid cooling supply system 12 and are coupled to a treatment device 20 which may be positioned inside a patient 64. The supply path 66 originates at the fluid reservoir 22, extends through the heat exchanger 28, then through the pump 30 before extending into the patient 64 and coupled to the treatment device 20. The return path 68 originates at the treatment device 20 and terminates at the fluid reservoir 22 for recirculation of the fluid through the system 101. Alternatively, the return path 68 may be coupled to a waste reservoir 67 in an open loop system.

In the illustrated example, the pump 30 draws fluid from the fluid reservoir 22 and through the heat exchanger 28 at a negative pressure. The fluid is chilled by the cooling device 36 as it travels through the heat exchanger 28. The fluid is then supplied to the treatment device 20 by the pump 30 at a positive pressure via the supply path 66. The fluid is circulated through the treatment device 20 and returned from the treatment device 20. In some aspects, the heat exchanger 28 may include the fluid reservoir 22 inside the fluid exchanger 28 (FIG. 6C).

In this example, the pump 30 includes a forward gear and a reverse gear, as depicted by arrows P. The forward gear draws the fluid from the fluid reservoir 22 and through the heat exchanger 28 to circulate chilled fluid through the treatment device 20. Conversely, the reverse gear pushes the fluid in reverse through the heat exchanger 28 to expel gas that may exist in portions of the system 101. In some aspects, the pump 30 is coupled to a controller for variable control over the speed of the pump in order to control the amount of fluid delivery to the treatment device. Thus, the size and apposition pressure of the treatment device may be controlled by the variable speed controller. Moreover, a non-contact pressure measurement device may be electrically coupled to the pump and positioned proximate the high pressure side of the fluid path to regulate system pressure, such as by varying the speed of the pump in response to the pressure measured by the non-contact pressure measurement device, for example.

In some aspects, a pump 30a is provided downstream of the treatment device 20 to draw the fluid from the treatment device 20. Accordingly, the pump 30 and the supplemental pump 30a cooperatively act to circulate chilled fluid through the system. The pump 30a may draw up to 14 psi of fluid pressure from the treatment device 20. Accordingly, the pressure downstream of the treatment device 20 may be lower, such as around 10-20 psi, while the pressure upstream the treatment device 20 may be higher, such as around 80-100 psi. Such configuration of providing an additional pump downstream a treatment device improves cooling at the treatment region in the patient because the flow rate is increased through the treatment device by virtue of simultaneously pushing the fluid with one pump while drawing the fluid with another pump. Furthermore, by drawing fluid from the treatment device 20 via the pump 30a, a lower fluid pressure may be exhibited in the treatment device 20 than without such additional pump. In some aspects, a pump 30a is the only pump or device circulating fluid through the system. Such configuration can further lower fluid pressure downstream of the treatment device.

FIG. 4 shows a treatment system 201 according to one aspect of the present disclosure. The treatment system 201 may include a fluid cooling supply system 12 and a pulmonary treatment system 19. The fluid cooling supply system 12 may be coupled to the pulmonary treatment system 19 by a supply line 14 and a return line 16. The pulmonary treatment system 19 may include a flexible bronchoscope 18 having a control portion 68, a steering mechanism 70, and a video system 72. The flexible bronchoscope 18 may include an insertion tube 74 extending from a control section 76 external to the patient's body, through the trachea 78, and to a treatment device 20 at a treatment site within the left main bronchus 80 of the lungs 81 of a patient. The treatment device 20 can be positioned in the left main bronchus 80, or positioned in other locations, such as within the right main bronchi, the lobar bronchi, and bronchus intermedius. The treatment device 20 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. Based on the effectiveness of the treatment, the physician can concurrently or sequentially treat additional lobe(s).

Figure 5:
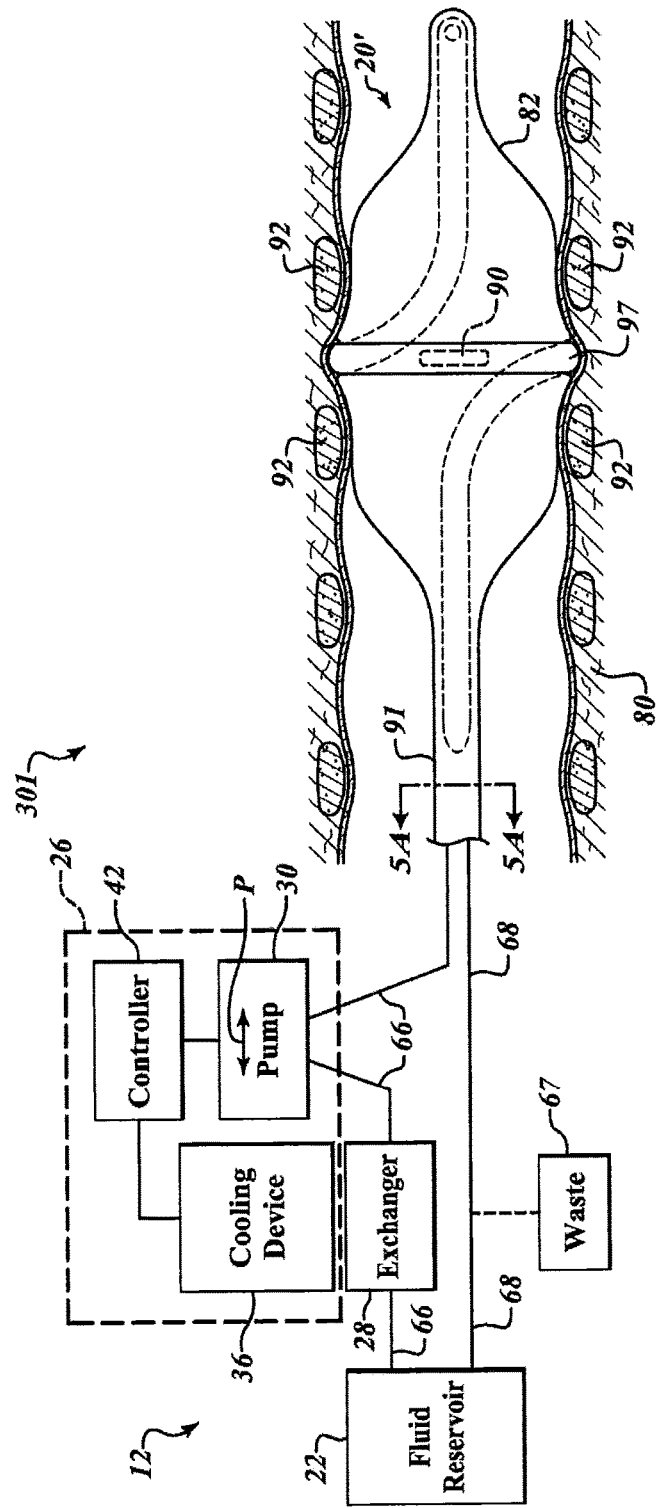
FIG. 5 is a schematic illustration of a fluid cooling delivery system coupled to an energy delivery device positioned in a patient during a treatment session according to one aspect.

The steering mechanism 70 may be coupled to the bronchoscope 18 and may receive the supply line 14 and the return line 16 to allow egress of the lines into the bronchoscope 18 and ultimately to the treatment device 20 (FIG. 5). The bronchoscope 18 may be coupled to the video system 72, which allows a practitioner to observe progress of the insertion tube 74 through the patient on a monitor 82 as the insertion tube 74 is steered with the assistance of the control portion 68. The video system 72 can allow a practitioner to determine whether fluid is supplied to the treatment device 20. The bronchoscope 18 may be coupled to the control portion 68 to control some or all aspects of treatment, such as the amount of energy delivered to the treatment device 20.

The fluid cooling supply system 12 may have the same or similar features as with the systems described with reference to FIGS. 1-3. The supply line 14 of the fluid cooling supply system 12 originates at a fluid reservoir 22 and through a heat exchanger 28 and through a pump 30. The supply line 14 extends through a damper 37 and then through the steering mechanism 70 for fluid supply to the treatment device 20. The return line 16 originates at the treatment device 20 and extends from the steering mechanism 70 and back to the fluid reservoir 22. Accordingly, the pump 30 may draw fluid from the fluid reservoir 22 and through the heat exchanger 28 while the fluid is chilled by the cooling device 36 (FIG. 3). The fluid may travel through a fluid channel 114 of the heat exchanger 28. The fluid may then be supplied to the treatment device 20 at a positive pressure via the supply line 14. The fluid may be circulated through the treatment device 20 and returned from the treatment device 20 to the fluid reservoir 22 in a closed loop system. The cooling device 36 and the pump 30 may be manually controlled by the controller devices 62.

FIG. 5 shows a treatment system 301 according to an aspect of the present disclosure. The system 301 includes a fluid cooling supply system 12 coupled to a treatment device 20' for circulating fluid through the treatment device 20' positioned in a patient. For purposes of illustration, the treatment device 20' is shown in a side elevation view positioned in a bronchus 80. By way of example, the schematic of the fluid cooling supply system 12 of FIG. 3 is shown having a supply path 66 and a return path 68 in fluid communication with the treatment device 20'. The fluid cooling supply system 12 is not described in detail with reference to FIG. 5 as it may include some or all of the same features as described with reference to FIG. 3 and with reference to FIG. 8, for example.

Figure 5A:
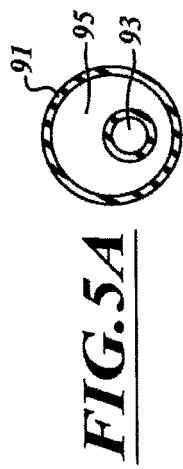
FIG. 5A is a cross-sectional view of the supply and return lumens of the treatment device of FIG. 5, taken along lines 5A-5A of FIG. 5.

In some aspects, the treatment device 20' includes an expandable member 82 that extends from a distal end of an elongate member 91. FIG. 5A shows a cross sectional view of the elongate member 91 taken along lines 5A-5A. The elongate member 91 may include a supply lumen 93 and a return lumen 95. The supply lumen 93 is in fluid communication with the supply path 66 of the fluid cooling supply system 12, and the return lumen 95 is in fluid communication with the return path 68. A fluid supply channel 97 also extends from the distal end of the elongate member 91, around a portion of the circumference of the expandable member 82, to a distal end of the expandable member 82. A proximal end of the fluid supply channel 97 is in fluid communication with the supply lumen 93, and a distal end of the fluid supply channel 97 is in fluid communication with the interior of the expandable member 82. The return lumen 95 is in fluid communication with the interior of the expandable member 82 at a proximal end of the expandable member 82. The return lumen 95 may surround the supply lumen 93 in the elongate member 91. The fluid in the supply lumen 93 is both at a higher pressure and a lower temperature than the cooling fluid in the return lumen 95. Advantageously, locating the supply lumen 93 within the return lumen 95 reduces the delivery size of the treatment device 20' and reduces thermal losses in the supply lumen 93. An electrode 90 is applied to an outside surface of the fluid supply channel 97 to form lesions 92 adjacent the bronchus 80 of a patient.

Fluid is circulated by the fluid cooling supply system 12 through the treatment device 20' during energy delivery to the electrode 90. The fluid is circulated serially from the supply lumen 93, through the fluid supply channel 97, into the expandable member 82, and then out the return lumen 95. Fluid circulating through the fluid supply channel 97 and the expandable member 82 protect a region of tissue between an interior wall of an airway and a target treatment region that is located within the airway wall and radially spaced from the interior wall of the airway. In this example, the treatment device 20 uses energy to damage target regions. As used herein, the term "energy" is broadly construed to include, without limitation, thermal energy, cryogenic energy (e.g., cooling energy), electrical energy, acoustic energy (e.g., ultrasonic energy), radio frequency energy, pulsed high voltage energy, mechanical energy, ionizing radiation, optical energy (e.g., light energy), microwave, and combinations thereof, as well as other types of energy suitable for treating tissue. In some embodiments, the treatment device delivers energy and one or more substances (e.g., radioactive seeds, radioactive materials, etc.), treatment agents, and the like. In the example shown in FIGS. 5 and 5A, the treatment device can include one or more electrodes 90 that are each operable to output ultrasound, microwave, electrical energy, and/or radiofrequency (RF) energy.

In some aspects, fluid is circulated by the fluid cooling supply system 12 directly adjacent the electrode 90. Accordingly, the supply and return lumens may be positioned adjacent the electrode 90, which may provide a high mass flow rate of chilled fluid across a surface of the electrode 90.

In another example, an energy delivery portion is located within an expandable member configured to circulate the cooled fluid. For example, an ultrasonic energy delivery device or microwave antennae can be located in an inflatable balloon through which the cooled fluid is circulated.

The continuous flow of chilled fluid through the energy delivery device allows the energy delivery portion to form much deeper lesions while delivering the same amount of energy through the tissue of the patient. Thus, treatment is quicker and more effective at the target regions than without providing continuous chilled fluid throughout the treatment device as described in the present disclosure because the nerve tissue at the target regions is more effectively and efficiently damaged.

As mentioned above, the heat exchanger discussed with reference to FIGS. 1-5B could instead be a resilient body, such as a bag, removably coupled to the cooling device with a given biasing force for effectuating heat transfer from fluid contained in or traveling through the bag. The bag may include the same or similar features as the cartridges discussed herein. For example, the bag may have a fluid channel having a serpentine pattern. The bag may have an outlet port in fluid communication with a treatment device positioned in a patient. At least one biasing mechanism may be coupled to the bag and configured to bias the bag with a given force to chill the fluid to a selected temperature for delivery of a patient, such as further described elsewhere in the present disclosure. The at least on biasing mechanism may be a plate removably attached to the cooling device such that the bag is positioned between the cooling device and the plate, or the bag may be biased to the cooling device by other attachment devices, such as with clamps or other devices exhibiting biasing forces to an object. The bag may include a membrane positioned adjacent a cooling device and having a thickness of between 2 millimeters and 4 millimeters, although the thickness may be less than 2 millimeters depending upon the material of the bag. In addition, the bag may be positioned horizontal over a cooling device and the weight, such as a metal plate, may be positioned over the bag to provide a sufficient biasing force to cool the fluid to a desired fluid temperature. The given biasing force between the bag and the cooling device may be between 5 and 10 pounds of force, or may vary beyond such range.

In other embodiments, a cartridge and a bag may be used together. For example, a cartridge may have a slot to receive a bag configured to contain a fluid. The bag may be inserted into the slot and the fluid may be inserted into the bag, thereby inflating the bag in the slot, which provides a sufficient given biasing force between the bag and a thermal surface of the cartridge to effectuate heat transfer of the fluid by a cooling device against which the cartridge is positioned adjacent thereto, for example.

FIGS. 6A and 6B show a heat exchanger cartridge 28 according to one aspect of the present disclosure. FIG. 6A shows the cartridge 28 having a first plate 41 and a second plate 43 secured to each other. The first plate 41 is preferably comprised of a thermally conductive material, such as copper, and includes a thermally conductive surface 98 for biasing to a cooling device 36 (FIGS. 1 and 2). The first plate 41 may include 0.5 to 1 micron of silver material over the copper material to improve thermal transfer between the fluid in the heat exchanger cartridge 28 and the cooling device 36. This also provides a biocompatible and inert surface for the fluid to contact in the heat exchanger cartridge 28. The second plate 43 is preferably comprised of an insulating material, such as a polymer, ABS, nylon, or polycarbonate. An insulating foam or natural cork insulator could be placed inside the cartridge 28 or on an outer surface of the cartridge 28 to thermally isolate the fluid from the ambient air temperature around the cartridge 28.

The cartridge 28 may have at least one biasing mechanism that may include four magnets 99 secured to the cartridge. The magnets 99 may be secured into bores 100 at respective corners of the second plate 43. Alternatively, one long magnet or a plurality of magnets can be secured along various portions of the cartridge to achieve the same biasing force to a cooling device as further discussed in the present disclosure. Securing the magnets 99 at the four corners of the cartridge 28 provides improved surface-to-surface contact between the thermally conductive surface 98 of the first plate 41 and the thermal plate 38 of the cooling device 36 because the magnets tend to provide uniform biasing force along most or all of the surface area of the thermally conductive surface 98 as biased to the thermal plate 38, thereby improving and maintaining consistent and efficient heat transfer from the fluid during treatments (FIG. 7B).

The cartridge 28 further includes an inlet port 102 positioned at an upper portion 104 of a first end 106 of the second plate 43, and an outlet port 108 positioned at a lower portion 110 of a second end 112 of the second plate 43. The inlet port 102 may be coupleable to a fluid reservoir, and the outlet port 108 may be coupleable to a treatment device positioned in a patient.

With continued reference to FIG. 6B, the second plate 43 includes a fluid channel 114 in fluid communication with the inlet port 102 and the outlet port 108. The fluid channel 114 serpentines throughout the cartridge in a vertical manner from the upper portion 104 to the lower portion 110 such that any gas in the system may tend to rise toward the upper portion of the fluid channel 114. The fluid channel 114 is formed to have a substantially flat cross sectional area through which fluid is traversed (FIG. 6D). This provides one advantage of improving heat transfer from the fluid during treatment because the fluid traverses adjacent the first plate 41 in a substantially thin or flat manner, which can maximize the heat transfer from the fluid by virtue of thermodynamic principles. The second plate 43 further includes a perimeter recess 116 that is formed to receive the first plate 41 such that the thermally conductive surface 98 is substantially flush and planar with a biasing surface 118 of the second plate 43. The perimeter recess 116 may include sealing channels 120 that may receive an adhesive to secure the first plate 41 to the second plate 43 (FIGS. 6D and 6E). Accordingly, the first plate 41 may be secured to the second plate 43 across various portions of the first plate 41, which can prevent or reduce bulging or distortion of the first plate 41 due to suction forces or other forces. As a result, thermal heat transfer is increased because greater surface-to-surface contact is maintained between the first plate 41 and the thermal plate 38 due to the particular configuration of the cartridge.

FIG. 6C shows a heat exchanger cartridge 28' according to one aspect of the present disclosure. The cartridge 28' may include the same or similar features with reference to FIGS. 6A and 6B. The cartridge 28' includes a first plate 41' and a second plate 43' and four magnets 99 positioned in bores 100 at respective corners of the second plate 43'. Thus, the cartridge 28' includes many of the same or similar features discussed with reference to FIGS. 6A and 6B with at least one notable difference: the second plate 43' includes a fluid reservoir 122 contained wholly within a cavity 124 of the cartridge 28' such that there is no need for an external fluid reservoir to operate a fluid cooling supply system. From the fluid reservoir 122, a fluid channel 114' serpentines throughout the cartridge in a vertical manner from top to bottom such that any gas in the system may tend to rise to the upper portion of the fluid channel 114' and to the fluid reservoir 122. Providing a fluid reservoir 122 inside the cartridge 28' provides the advantage of improving sterility because it is no longer required to provide an external reservoir with various supply tubes and connections which a practitioner must handle and connect and disconnect between treatments. Providing a fluid reservoir 122 inside the cartridge 28' further provides the advantage of having a disposable cartridge that can be easily manufactured and supplied to practitioners for: quick attachment to a cooling device, sterile use of a fluid during treatment, and easy detachment and replacement of the cartridge between treatments. In some aspects, a small bag may be positioned in the cavity 124 and coupled to the fluid channel 114'. In this manner, fluid pressure remains constant in the fluid channel 114' during operation because the bag will collapse when fluid is drawn out of the bag.

In some embodiments, corner portions of the fluid channels in each cartridge discussed in the present disclosure may have a relatively large radius, such as illustrated by the shadow lines of a corner portion 121 on FIG. 6C. The corner portion 121 provides a gradual transition between horizontal and vertical sidewalls of the fluid channel to help overcome the surface tension of gas bubbles that may otherwise become stuck in the corners of the fluid channel. This will increase the fluid pressure in the cartridge because there will be less gas bubbles in the fluid channel than if the cartridge had corners with a smaller radius, for example.

FIG. 6D shows a cross sectional view of the heat exchanger cartridge 28 taken along lines 6D-6D of FIG. 6A. FIG. 6E show a portion of FIG. 6D. The features shown in FIGS. 6D and 6E may include the same or similar features with reference to FIG. 6C. The cartridge 28 includes a first plate 41 and a second plate 43 secured to each other. The second plate 43 includes a fluid channel 114 that serpentines through the cartridge 28 adjacent the first plate 43. The second plate 43 includes a perimeter recess 116 and sealing channels 120 that may receive an adhesive to secure the first plate 41 to the second plate 43. Accordingly, the first plate 41 may be secured to the second plate 43 across various portions of the first plate 41, which can prevent or reduce distortion of the first plate 41 due to suction forces or other forces. The configuration shown and discussed with reference to FIGS. 1-5 allows for a relatively thin first plate 41 (as further discussed herein), which improves heat transfer from the fluid in the fluid channel 114 chilling of the fluid.

The first plate 41 may have a thickness T to maintain a substantially flat surface between the cartridge 28 and the thermal plate 38. If the first plate 41 is too thin for a specified metal, when place under vacuum, the first plate 41 may exhibit a rippled surface at locations along which the fluid channel 114 is positioned. This may create air pockets between thermally conductive surface 41 and the planar surface 51 of the thermal plate 38, which thereby results in poor heat transfer from the fluid. In some embodiments, the thickness T of the first plate 41 is between 0.005 inch and 0.01 inch, but the thickness T may vary beyond such range. Preferably, the thickness T it is 0.01 inch.

In addition, a cross sectional profile of the fluid channel 114 may include a corner R having a radius (FIG. 6E), as compared to having a right angle profile (FIG. 6D). Corner R is shown at a lower corner portion of the fluid channel for purposes of illustration; corner R is ideally formed at upper portions of the fluid channel to prevent gas bubbles from being trapped in the otherwise right angled corners, particularly near the upper corners where the fluid channel transitions from one vertical channel section to a horizontal channel section (FIG. 6C). Providing rounded corners may increase the fluid pressure in the cartridge because there would be less gas bubbles in the fluid channel than if the channel had corners with a right angle, for example.

Figure 7A:
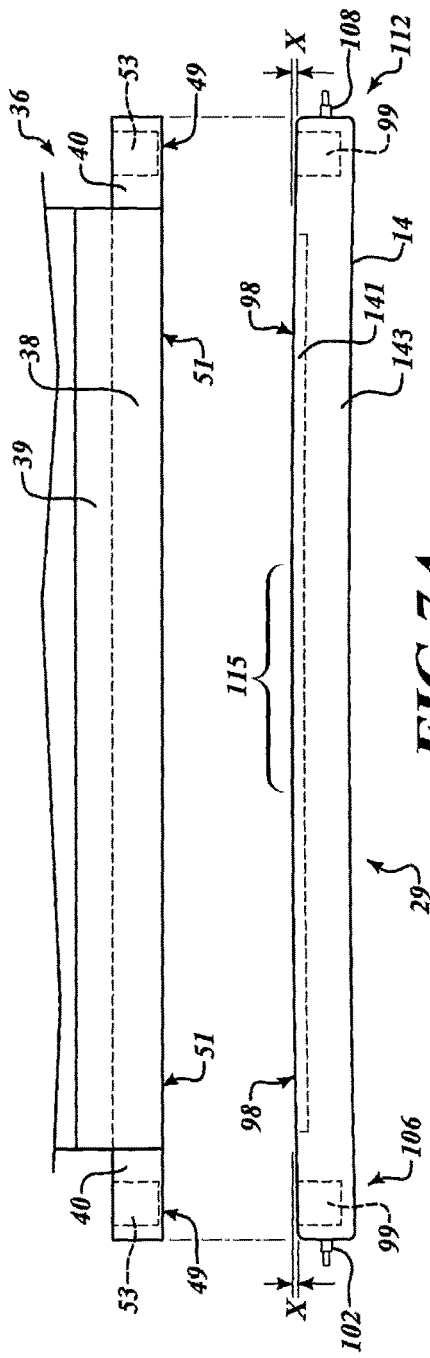
FIG. 7A is a side view of a heat exchanger according to one aspect, showing the cartridge in a first state disengaged from a cooling device.
Figure 7B:
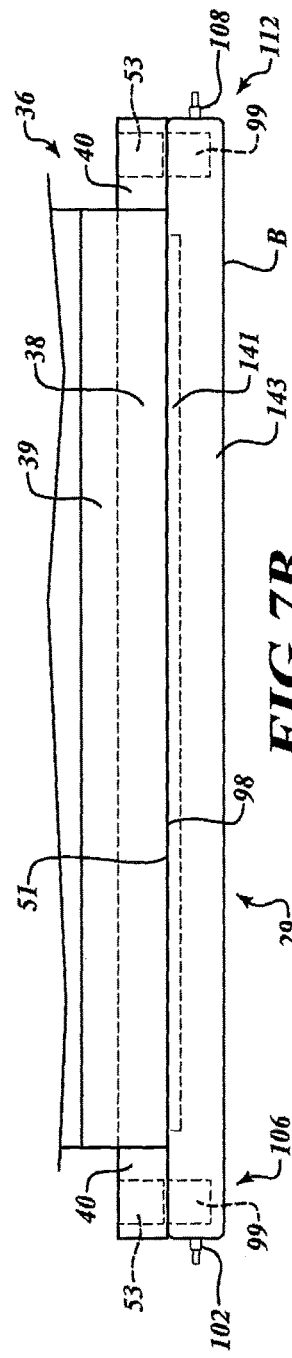
FIG. 7B is a side view of the heat exchanger of FIG. 7A, showing the heat exchanger in a second state and engaged to a cooling device.

FIGS. 7A and 7B show top plan views of a heat exchanger cartridge 28 according to one aspect. The cartridge 28 may have the same or similar features as the cartridges with reference to FIGS. 1-6E. Accordingly, the cartridge may include a first plate 141 and a second plate 143 secured to each other. The first plate 141 may include a thermally conductive surface 98. Magnets 99 may be secured to the cartridge 28 at opposing ends of the cartridge 28. Likewise, a cooling device 36 having a thermal plate 38 and a hot plate 39 may also have the same or similar features as described with reference to FIGS. 1-4. The thermal plate 38 includes a planar surface 51 to bias against the thermally conductive surface 98 of the cartridge 29. A spacer 40 may extend around a perimeter of the thermal plate 38 and the hot plate 39 (FIG. 2). The spacer 40 may include magnets 53 positioned at corresponding positions relative to the cartridge magnets 99. The spacer 40 may include an outer surface 49 that is substantially planar with the planar surface 51 of the thermal plate 38 to collectively provide a flush surface region over which the cartridge 28 may be biased.

The cartridge 28 may be manufactured or formed to be in a first state A when disengaged from the thermal plate 38 (FIG. 7A) and to be in a second state B when engaged to the thermal plate 38 (FIG. 7B). Accordingly, FIG. 7A shows the cartridge 28 in the first state A (a pre-stressed configuration), which is achieved by forming the first plate 141 and the second plate 143 of the cartridge 28 to have a profile with a convex shape relative to the planar surface 51 of the thermal plate 38. As such, a first end 106 and a second end 112 of the cartridge 28 may be positioned slightly farther away from a central area 115 of the cartridge, which is illustrated by distances X shown on ends 106, 112 of the cartridge 28. As shown in FIG. 7B, when the cartridge 28 is engaged to the cooling device 36, because of the pre-stressed shape and magnetic force the cartridge 28 is biased flush to the thermal plate 38. Thus, the cartridge 28 has a profile that is a substantially flat relative to the thermal plate 38 because the cartridge 28 tends to flatten due to magnetic forces. Such configuration and biasing means provide improved surface-to-surface contact between the thermally conductive surface 98 of the first plate 141 and the thermal plate 38 of the cooling device 36, thereby resulting in improved heat transfer while reducing heat losses. Improving heat transfer and reducing heat losses is important during treatment of a patient because some treatment systems, such as the pulmonary treatment system discussed in the present disclosure, may require a given fluid temperature and a given fluid pressure for a given amount of time during treatment.

Figure 8:
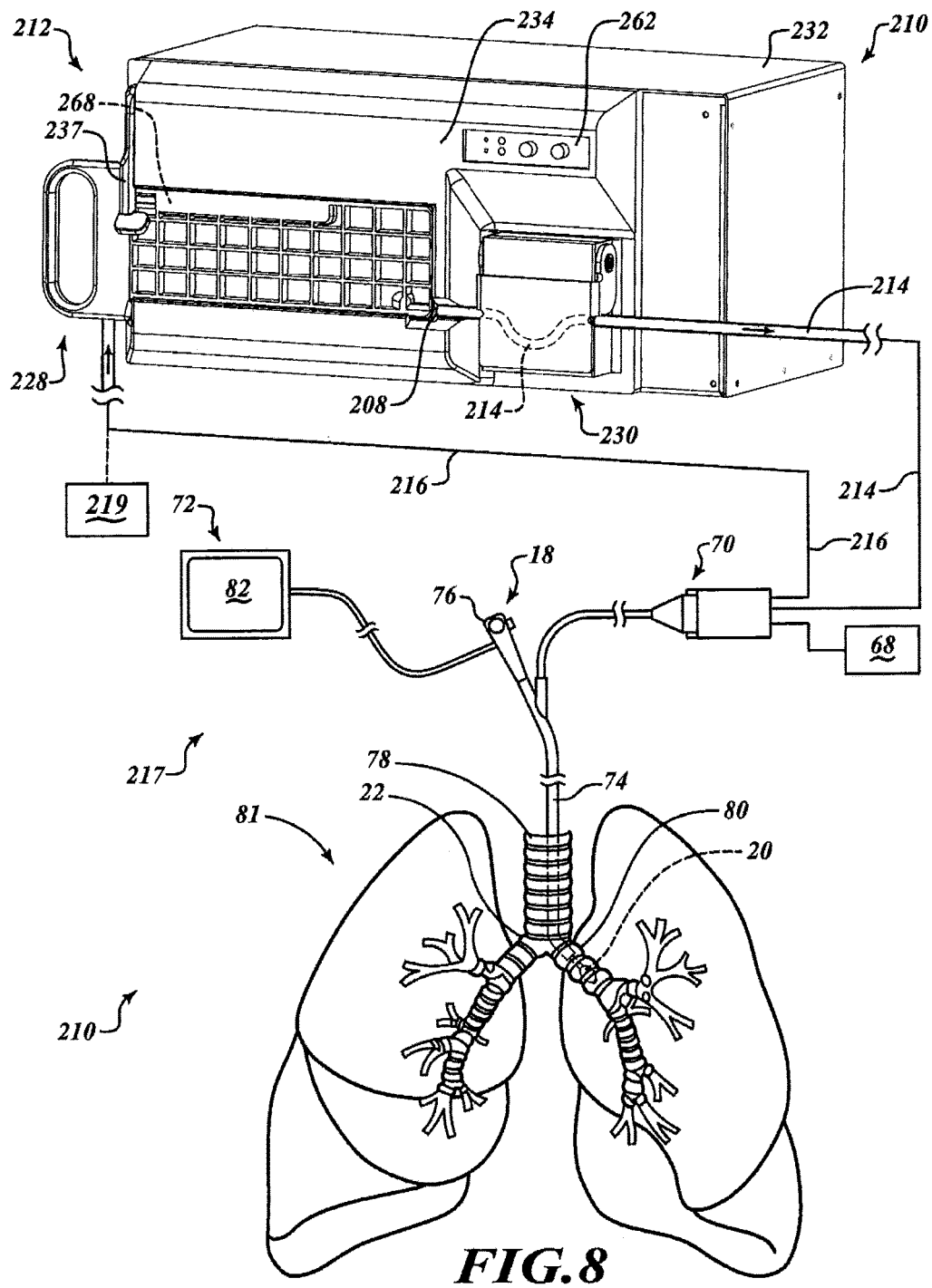
FIG. 8 is a perspective view of a fluid cooling delivery system during a treatment session according to one aspect.
Figure 9:
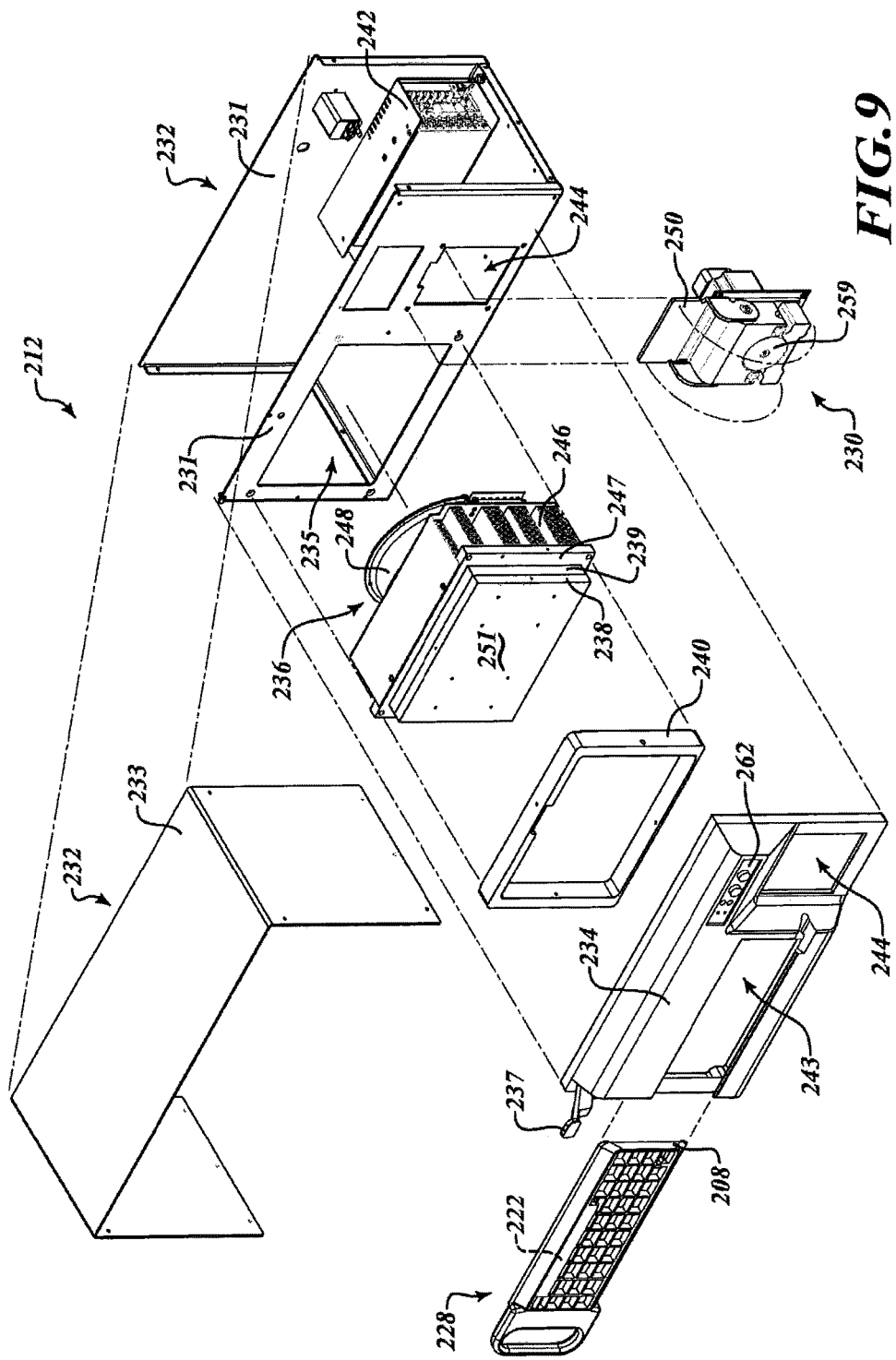
FIG. 9 is a partially exploded view of a fluid cooling delivery system according to one aspect.

FIGS. 8 and 9 illustrate a treatment system 210 according to one aspect of the present disclosure. FIG. 8 shows the treatment system 210 having a fluid cooling supply system 212 and a pulmonary treatment system 217 coupled to each other by a supply line 214 and a return line 216. FIG. 9 shows a partially exploded view of certain components of the fluid cooling supply system 12 of FIG. 8.

The treatment system 210 shown in FIGS. 8-13B may have the same or similar features of the systems described and shown with reference to FIGS. 1-7B. Accordingly, the pulmonary treatment system 217 may include a flexible bronchoscope 18 having a treatment device 20, a control portion 68, a steering mechanism 70, and a video system 72. The flexible bronchoscope 18 may include an insertion tube 74 extending from a control section 76 external to the patient's body, through the trachea 78, and to a treatment site within the left main bronchus 80 of the lungs 81 of a patient. The treatment device 20 can be positioned in the left main bronchus 80, or positioned in other locations, such as within the right main bronchi, the lobar bronchi, and bronchus intermedius. The treatment device 20 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. Based on the effectiveness of the treatment, the physician can concurrently or sequentially treat additional lobe(s).

The steering mechanism 70 may be coupled to the bronchoscope 18 and may receive the supply line 214 and the return line 216 to allow egress of the lines into the bronchoscope 18 and ultimately to the treatment device 20. The bronchoscope 18 may be coupled to the video system 72, which allows a practitioner to observe progress of the insertion tube 74 through the patient on a monitor 82 as the insertion tube 74 is steered with the assistance of the control portion 68. The video system 72 can also allow a practitioner to determine whether fluid is supplied to the treatment device 20 from the fluid cooling supply system 212. In addition, the bronchoscope 18 may be coupled to the control portion 68 to control some or all aspects of treatment, such as the amount of energy delivered to the treatment device 20. Accordingly, the treatment device 20 of the bronchoscope 18 is in fluid communication with the supply line 214 and the return line 216 of the fluid cooling supply system 212. As such, the fluid cooling supply system 212 is adapted to cool a fluid, pump the fluid, and circulate the fluid through the treatment device 20.

With continued reference to FIGS. 8 and 9, in some aspects the fluid cooling supply system 212 may include: a housing 232 having a front plate 234; a cooling device 236 having a thermal plate 238 extending through the front plate 234; a pump 230 for pumping fluid; a heat exchanger cartridge 228 coupled to the front plate 234 and biased to the cooling device 236; a cam system 237 coupled to the front plate 234 for biasing the cartridge 228 to the thermal plate 238; and a controller 242 coupled to the pump 230 and cooling device 236.

The housing 232 may include a first portion 231 and second portion 233 secured to each other and to structurally support and house various components of the system. The first portion 231 may include an opening 235 for receiving and supporting a front portion of the cooling device 236. The cooling device 236 includes the thermal plate 238, a hot plate 239, fins 246, and a fan 248, as with commonly available TECs. The thermal plate 238 may include a planar surface 251 for biasing to the cartridge 228. The cooling device 236 may include a support plate 247 secured to the first portion 231 of the housing 232. A spacer 240 may be secured between the cooling device 236 and the front plate 234 for additional support of the cooling device 236 and to allow egress of the thermal plate 238 through the front plate 234.

Figure 11A:
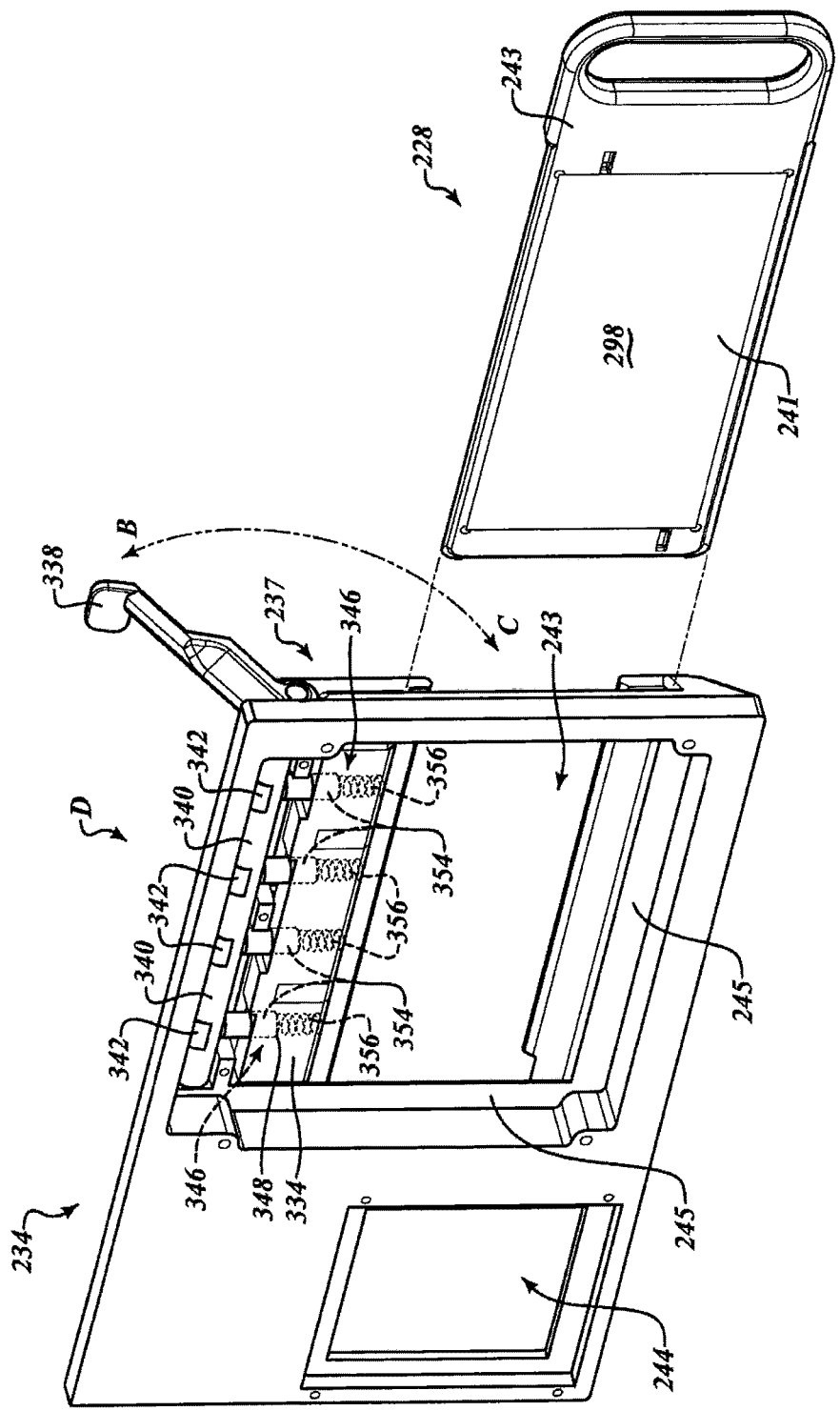
FIG. 11A is a back side perspective view of a portion of a fluid cooling delivery system according to one aspect, showing a cam system disengaged and a heat exchanger removed.
Figure 11B:
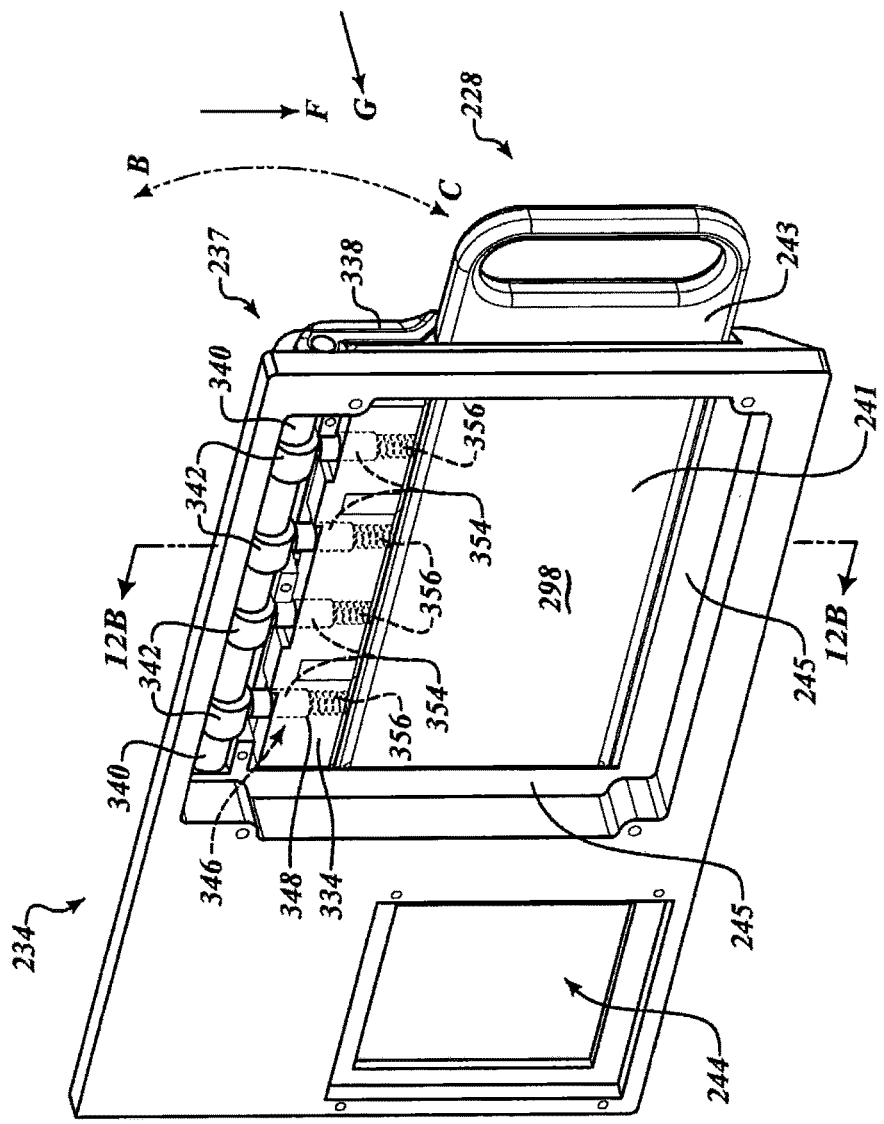
FIG. 11B is the back side perspective view of FIG. 11A, showing the cam system engaged and the heat exchanger installed.

In some aspects, the cartridge 228 is slideably coupled to the front plate 234 and biased against the thermal plate 238 of the cooling device 236 (FIGS. 11A and 11B). As further discussed below, the cartridge 228 may include a fluid reservoir 222 contained within the cartridge 228, or the system may have an external fluid reservoir outside of the cartridge 228 and in fluid communication with the cartridge 228. In the aspect shown, the cartridge includes an outlet port 208 coupled to the supply line 214. The supply line 214 is further coupled along the pump 230 and then through the bronchoscope 18 and to the treatment device 20 in the patient. Accordingly, the supply line 214 is in fluid communication with the treatment device 20, and the return line 216, also in fluid communication with the treatment device 20, extends from the insertion tube 74 and back to the cartridge 228 for recirculation of the fluid during treatment in a closed loop system. Alternatively, the return line 216 may extend to a waste reservoir 219 in an open loop system.

With continued reference to FIG. 9, the front plate 234 is attached to the front portion 231 of the housing 232. The front plate 234 and the housing 232 cooperate to structurally support the cooling device 236 and the pump 230. The front plate 234 includes an opening 243 for receiving the thermal plate 238 of the cooling device 236 and for facilitating biasing of the cartridge 228 to the cooling device 236. The front plate 234 may include an opening 244 for receiving a portion of the pump 230. The pump 230 may include a cover 250 and a rotating device 259 for coupling to the supply line 214. Importantly, the pump 230 is positioned downstream of the cartridge 228 such that the fluid in the cartridge 228 experiences a negative fluid pressure and such that the fluid supplied to the treatment device 20 experiences a positive fluid pressure during normal operation of the treatment system. The front plate 234 may include control devices 262 coupled to the controller 242 for controlling aspects of the system. The controller 242 may be coupled to the pump 230 for regulating the speed and direction of the pump 230, thereby regulating the direction of flow and volume of fluid circulating through the system. The controller 242 may also be coupled to the cooling device 236 to regulate the temperature of the fluid in the cartridge 228, thereby further regulating the temperature of the fluid circulating through the treatment device 20, and thereby regulating the temperature of patient tissue during treatment. It will be appreciated that the treatment device 20 discussed with reference to FIGS. 8 and 9 may include the same or similar features discussed with reference to FIGS. 1-7B, and particularly with reference to FIG. 5.

Figure 10:
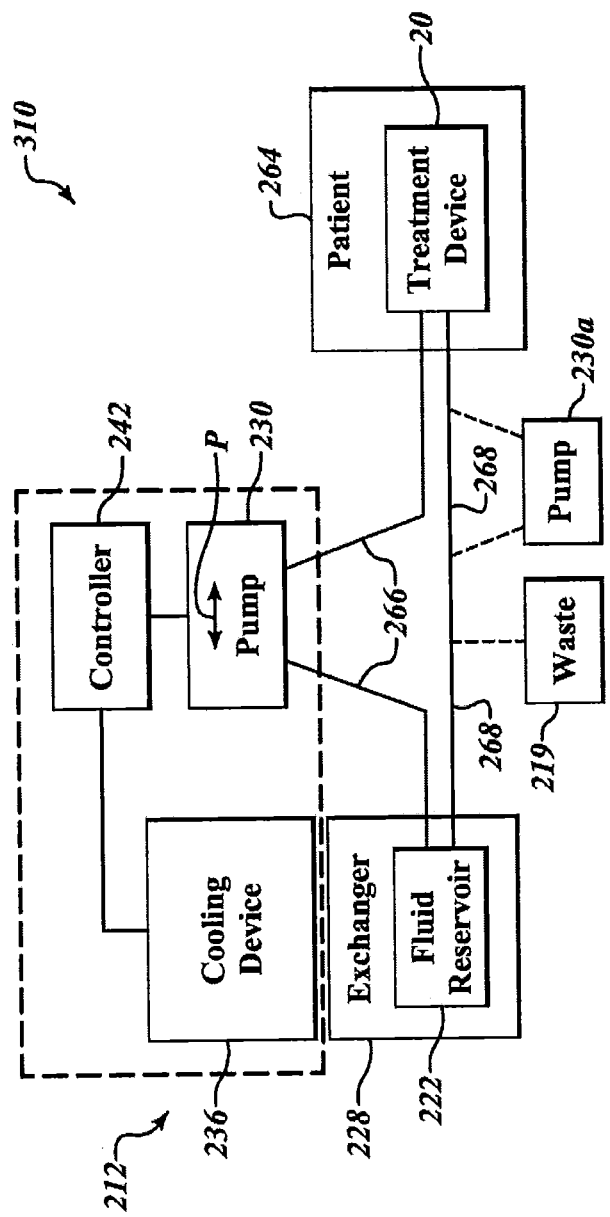
FIG. 10 is a schematic illustration of a fluid cooling delivery system during a treatment session according to one aspect.

FIG. 10 shows a schematic of a treatment system 310 according to one aspect, which may include some or all of the features of FIGS. 8 and 9. The treatment system 310 includes a fluid cooling supply system 212 coupled to a treatment device 20 positioned in a patient 264. The fluid cooling supply system 212 includes a cooling device 236, a heat exchanger 228, a pump 230, and a controller 242. The controller 242 may be coupled to the cooling device 236 and the pump 230 to regulate temperature and fluid circulation. The heat exchanger 228 may be removably coupled to the cooling device 236. A supply path 266 originates at a fluid reservoir 222 contained wholly within the heat exchanger 228. The supply path 266 extends through the heat exchanger 228 and through the pump 230 and terminates at the treatment device 20 for supplying chilled fluid to the patient 264. The return path 268 originates at the treatment device 20 and may return either to the fluid reservoir 222 for recirculation or to a waste reservoir 219. Accordingly, the fluid may be drawn from the reservoir 222 through the heat exchanger 228 at a negative pressure by the pump 230. The fluid is chilled by the cooling device 236 as it travels through the heat exchanger 228. The fluid is supplied to the treatment device 20 at a positive pressure by the pump 230. The fluid may then be circulated through the treatment device 20 and returned from the treatment device 20 to outside the patient 264.

The pump 230 may include forward and reverse gears, as depicted by arrows P, to draw and push the fluid forward through the heat exchanger 228 during treatment. The forward gear draws fluid from the heat exchanger 228 during normal operation of the system 310. Conversely, the reverse gear may push the fluid in reverse through the heat exchanger 228 to expel gas that may exist in the system 310. The speed and direction of the pump 230 may be controlled by the controller 242.

In some aspects, the pump 230 is coupled to a controller for variable control over the speed of the pump in order to control the amount of fluid delivery to the treatment device. Thus, the size and apposition pressure of the treatment device may be controlled by the variable speed controller. Moreover, a non-contact pressure measurement device may be electrically coupled to the pump and positioned proximate the high pressure side of the fluid path to regulate system pressure, such as by varying the speed of the pump in response to the pressure measured by the non-contact pressure measurement device, for example.

Figure 12A:
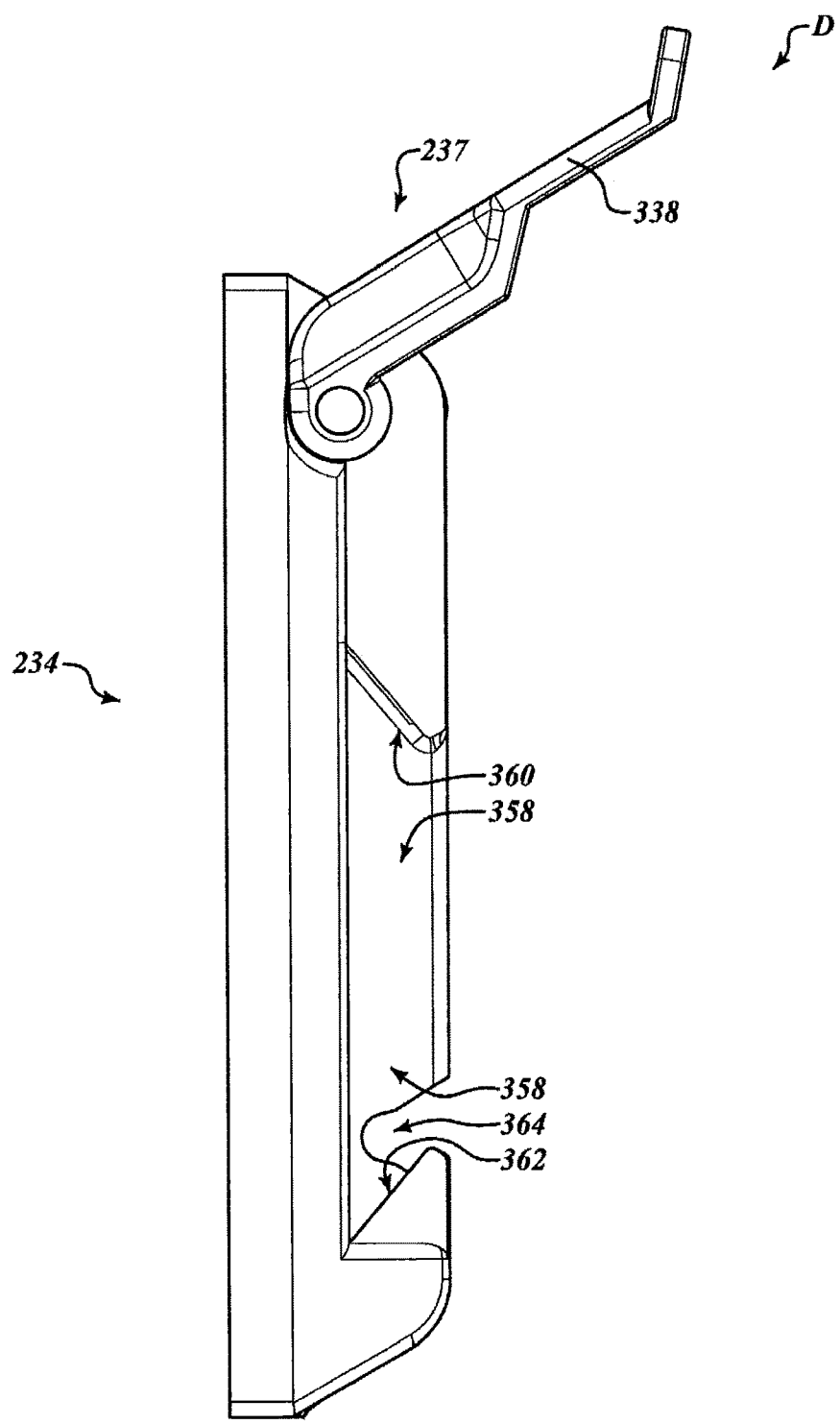
FIG. 12A is side view of the front plate of FIG. 11A according to one aspect.
Figure 12B:
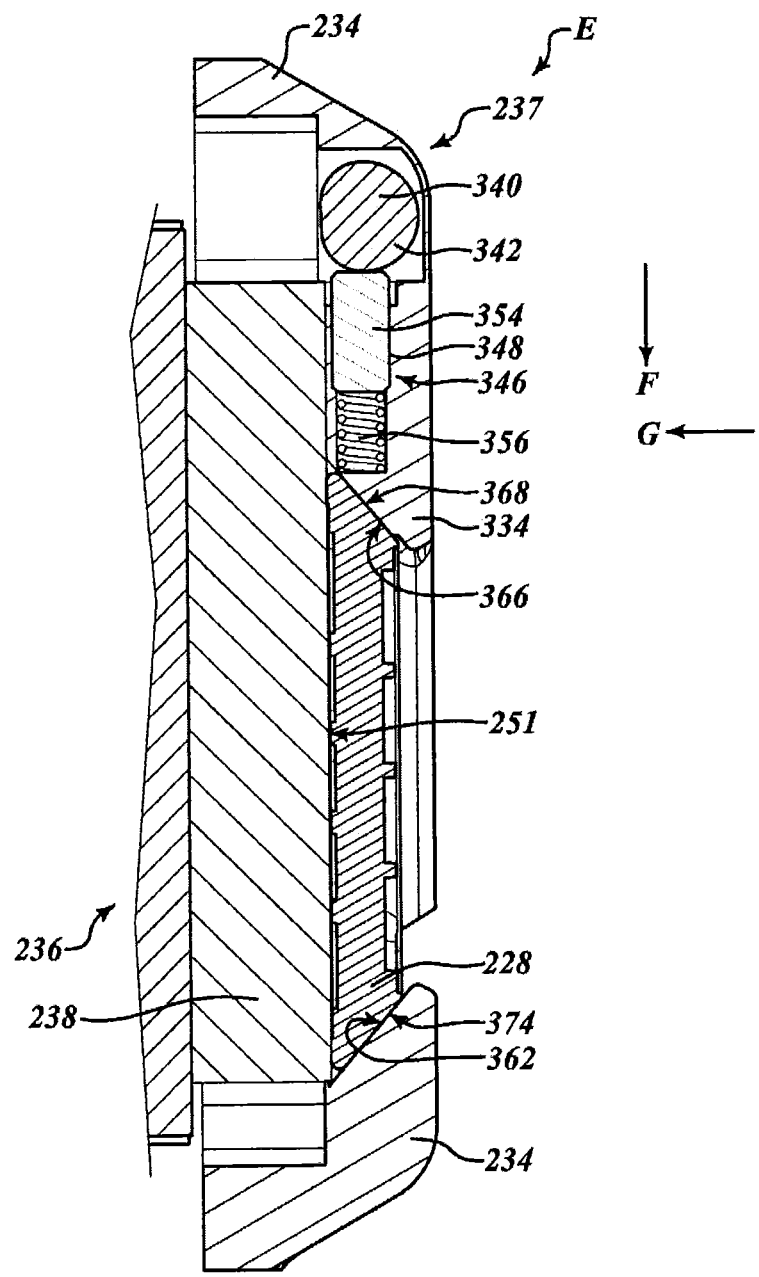
FIG. 12B is a side cross sectional view of a portion of a fluid cooling delivery system of FIG. 11B, taken along lines 12B-12B of FIG. 11B.
Figure 13A:
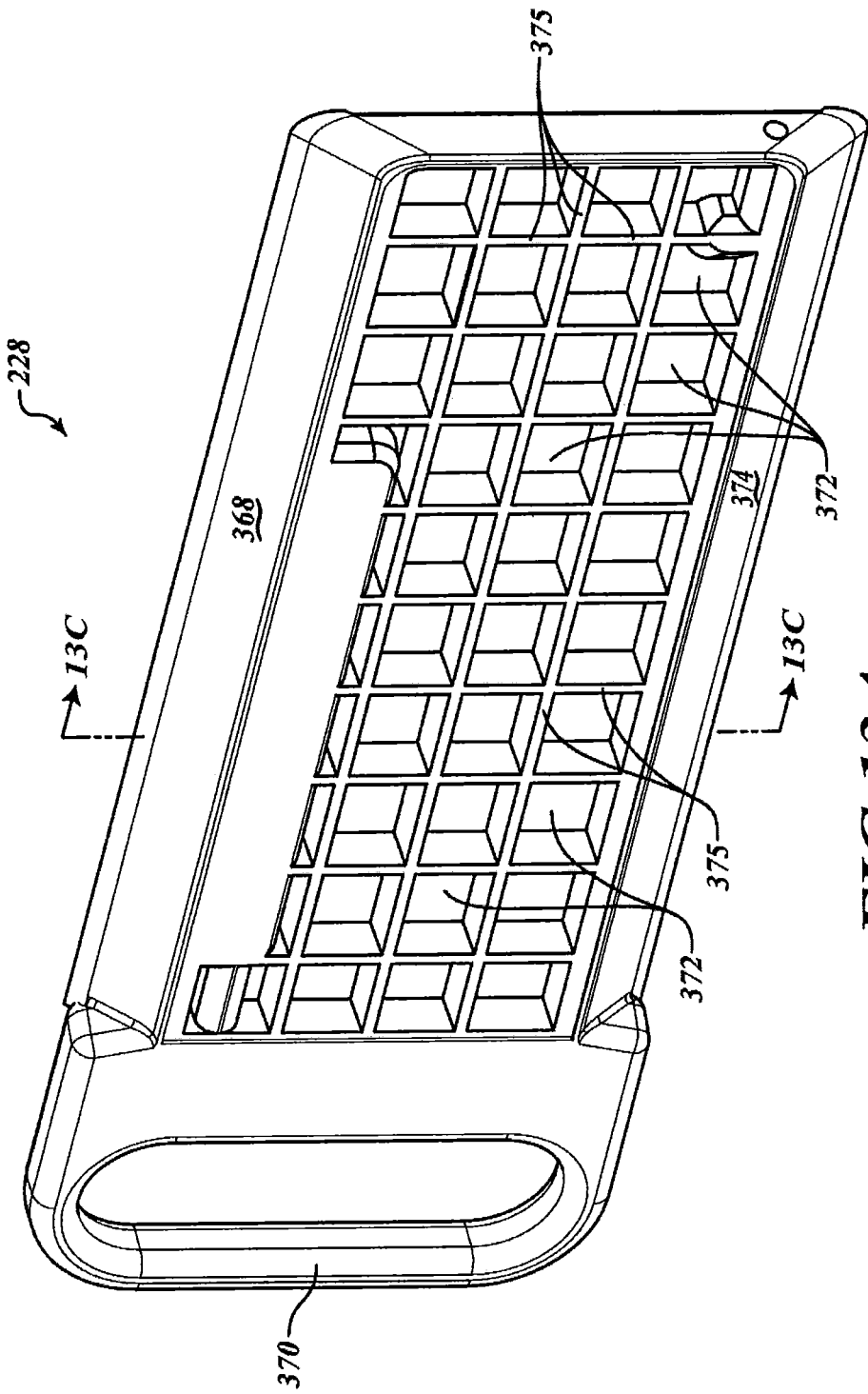
FIG. 13A is an isometric view of the heat exchanger cartridge of FIG. 11A.
Figure 13B:
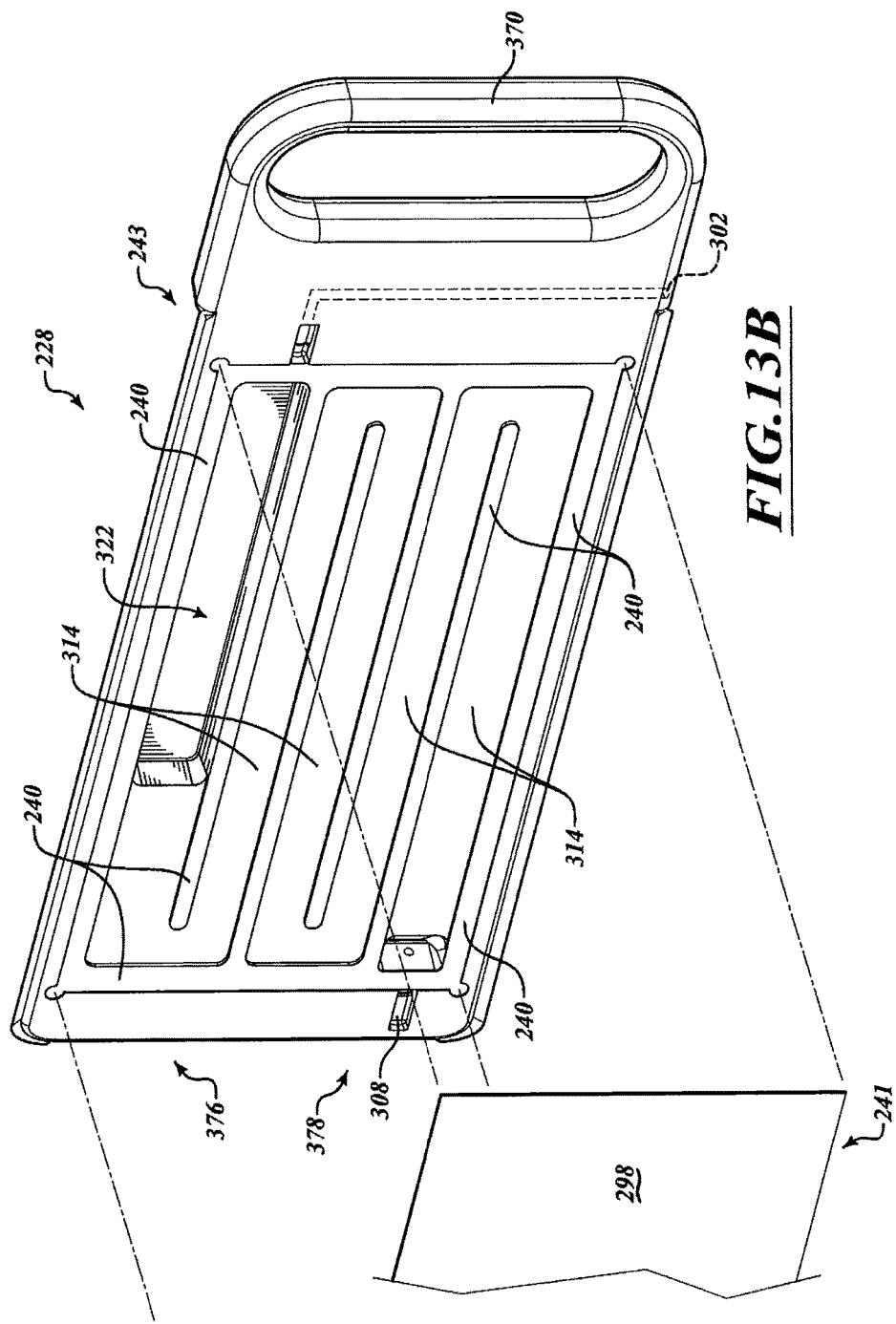
FIG. 13B is an inside perspective view of the heat exchanger of FIG. 11A.
Figure 13C:
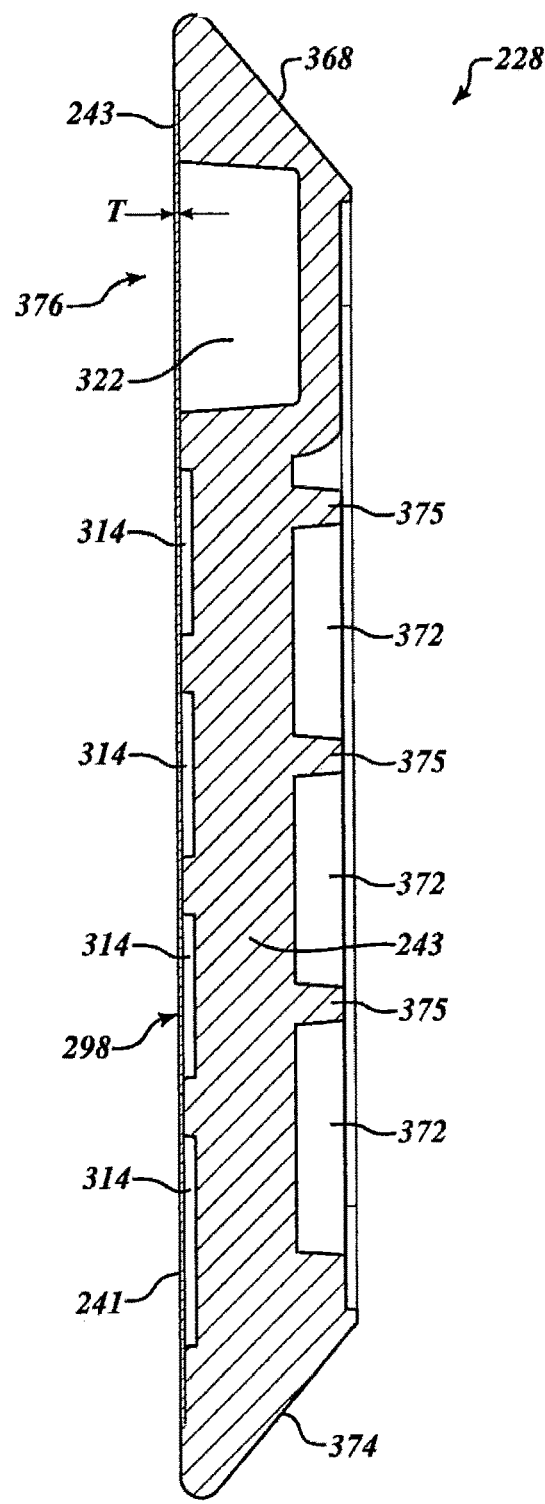
FIG. 13C is a cross sectional view of the heat exchanger of FIG. 13A, taken along lines 13C-13C of FIG. 13A.

FIGS. 11A-13C show certain aspects of the front plate 234, the cam system 237, and the cartridge 228 of a fluid cooling supply system 212. FIGS. 11A and 11B show a back perspective view of the front plate 234 and cartridge 228. The front plate may include a cam system 237 that, when actuated between an engaged state E and a disengaged state D, allows for removal of the cartridge 228. FIG. 12A shows a side elevational view of the front plate 234 and FIG. 12B shows a cross sectional view of the front plate 234, the cam system 237, the cartridge 228, and the cooling device 236, taken along lines 12B-12B of FIG. 11B. FIGS. 13A-13C show various views of the cartridge 228.

With continued reference to FIGS. 11A and 11B, the cartridge 228 includes a first plate 241 and a second plate 243 secured to each other. The first plate 241 includes a thermally conductive surface 298 for biasing to a thermal plate of a cooling device (FIGS. 9 and 12B). The front plate 234 includes an opening 243 and a receiving surface 245. The opening 243 may be sized to facilitate biasing of the cartridge 228 to the thermal plate of a cooling device 236. The receiving surface 245 is sized to receive a portion of the cooling device 236 such that the thermal plate 238 may extend partially through the opening 243. The front plate 234 may also have an opening 244 to receive a pump for pumping fluid through the cartridge 228. The front plate 234 may contain and support the cam system 237 for biasing the cartridge 228 to the cooling device. In some configurations, the cam system 237 includes a cam lever 338 coupled to a cam shaft 340 having four cam lobes 342. The cam lever 338 may be directly attached to the cam shaft 340, or it may be dynamically linked to the cam shaft 340 in other configurations. The four cam lobes 342 are formed along a length of the cam shaft 340 and spatially separated from each other. The cam system 237 may include an actuation member 344 and actuation devices 346. Each actuation device 346 may be comprised of a piston rod 354 and a spring 356 positioned below respective piston rods 354. The actuation devices 346 may be at least partially positioned in respective bores 348 of the actuation member 344 and may be positioned adjacent respective cam lobes 342 (FIG. 12B) such that rotation of the cam lobes 342 actuates the pistons 354 in a downward direction.

When the cam system 237 is in the disengaged state D, the cam system 237 is positioned to allow the front plate 234 to slideably receive the cartridge 228. Once the cartridge 228 fully engaged into the front plate 234, the cam system 237 may be actuated to the engaged state E by rotating the cam lever 338 and cam shaft 340 in a downward rotational direction depicted by arrow C in order to secure the cartridge 228 in the front plate 234 and to bias cartridge 228 to the thermal plate 38 of the cooling device 236 (FIG. 12B). Thus, when moved to the engaged state E, the cam lobes 342 simultaneously bias against respective piston rods 354 of the actuation devices 346, which tends to force the actuation devices 346 downwardly in a direction depicted by arrow F, which tends to force the actuation member 344 against the cartridge 228 approximately in a direction depicted by arrow G, which is further discussed below (FIG. 12B). Conversely, when the cam system 237 is moved from the engaged state E to the disengaged state D for removal of the cartridge 228, by virtue of actuating the cam lever 338 in a direction depicted by arrow B, the cam shaft 340 and cam lobes 342 rotate in a similar direction, which tends to remove the force applied to the actuation devices 346, which tends to remove the force applied by the actuation member 344 so that the cartridge 228 may be removed (FIG. 11A). As previously discussed, providing a given and sufficient biasing force between the cartridge and a cooling device improves surface-to-surface contact between the cartridge and the cooling device, which aids in the effective and efficient cooling of fluid traversing through the cartridge for supply to a patient.

FIG. 12A shows a left side elevation view of the front plate 234 of FIG. 11A according to one aspect of the present disclosure. The front plate 234 including a slot 358 sized to loosely receive a cartridge 228 when the cam system 237 is in the disengaged state D. The front plate 234 includes an upper biasing surface 360 and a lower biasing surface 362 sized to closely receive the cartridge 228. The upper biasing surface 360 is formed at an angle that is substantially non-parallel to the planar surface 251 of the thermal plate 238 (FIG. 12B). Likewise, the lower biasing surface 362 is formed at an angle that is substantially non-parallel to the planar surface 251 of the thermal plate 238. Thus, the slot 358 may have a trapezoid-shaped cross sectional profile to receive the cartridge 228, and the cartridge 228 may also have a corresponding trapezoid-shaped cross sectional profile (FIG. 13C). FIG. 12A further shows the cam lever 338 in the disengaged state D and a recess portion 364 for allowing passage of a supply line 214 (FIGS. 8 and 9).

FIG. 12B shows a cross sectional view of the front plate 234, the cartridge 228 positioned in the front plate 234, the cooling device 236 and thermal plate 238 positioned adjacent the cartridge 228, and the cam system 237 in the engaged state E. Regarding the cam system 237, the actuation member 344 includes a lower actuation surface 366 that is formed at an angle relative to the planar surface 251 of the thermal plate 238. As further discussed above, when engaging the cam system 237 via the cam lever 338 and the cam shaft 340, the cam lobes 342 force the actuation devices 346 downwardly and, therefore, the actuation devices 346 force the actuation member 344 downwardly in a direction depicted by arrow F. Consequently, the lower actuation surface 366 biases an upper angular surface 368 of the cartridge 228 and, simultaneously, the lower biasing surface 362 tends to bias a lower angular surface 374 of the cartridge 228, which tends to force the cartridge 228 inwardly in a direction depicted by arrow G. This configuration and operation results in the cartridge 228 biased in approximately a lateral direction against the thermal plate 238 with a given force to effectuate heat transfer from the fluid and to improve surface-to-surface contact between the cartridge 228 and the cooling device 236. This is accomplished, in part, because of the trapezoid-shaped profiles of the slot 358 and the cartridge 228 and because of the angular surface of the actuation member 344, which collectively tend to "slide" the cartridge 228 along respective angled surfaces and into position in the direction depicted by arrow G. Thus, the cam system 237, the front plate 234, and the cartridge 228 are sized to cooperatively operate to bias the cartridge 228 to the thermal plate 238 to effectuate heat transfer from the fluid contained in the cartridge 228.

FIG. 13A shows a front perspective view of a cartridge 228 according to one aspect of the present disclosure. The cartridge 228 includes a handle 370 positioned at a left end of the cartridge for easy insertion and removal of the cartridge 228 into the slot 358 of the front plate 234, as previously discussed. The cartridge 228 includes an upper angular surface 368 and a lower angular surface 374 that are formed at respective angles to permit insertion of the cartridge 228 into the front plate 234. The cartridge 228 further includes a plurality of cavities 372 defined by a plurality of cross members 375. The cavities 372 are sized and formed along the front portion cartridge to improve heat transfer from the fluid in the cartridge 228 during operation of the system.

FIG. 13B shows a back perspective view of a cartridge 228 according to one aspect of the present disclosure. The cartridge 228 includes a first plate 241 and a second plate 243 attached to each other. The first plate 241 is preferably comprised of a copper material and includes a thermally conductive surface 298 for biasing to a cooling device (FIG. 12B).). The first plate 241 may include 0.5 to 1 micron of silver material over the copper material to improve thermal transfer between the fluid in the heat exchanger cartridge 228 and the cooling device 236. This also provides a biocompatible and inert surface for the fluid to contact in the heat exchanger cartridge 228. The second plate 43 is preferably comprised of an insulating material, such as ABS, nylon, or polycarbonate. An insulating foam or natural cork insulator could be placed inside the cartridge 28 or on an outer surface of the cartridge 28 to thermally isolate the fluid from the ambient air temperature around the cartridge 28. The second plate 243 includes a fluid reservoir 322 positioned at an upper portion 376 of the cartridge 228. A fluid channel 314 is formed on the second plate 234 and is in fluid communication with the fluid reservoir 322. The fluid channel 314 serpentines throughout the cartridge in a vertical manner from top to bottom such that any gas in the system tends to rise to the upper portion 376 of the fluid channel 314 and into the fluid reservoir 322. The second plate 243 may include a sealing surface 240 that is recessed to receive the first plate 241. The sealing surface 240 may receive an adhesive to secure the first plate 241 to the second plate 243. Thus, the first plate 241 is secured to the second plate 243 across various portions of the first plate 241, which prevents distortion of the copper plate due to suction forces or other forces acting on the first plate 241.

The second plate 243 may include an outlet port 308 positioned at a lower portion 378 of the cartridge 228 and in fluid communication with the fluid channel 314 and the fluid reservoir 322. The outlet port 308 may be coupled to a supply line for supplying fluid to a patient. In some aspects, the cartridge 228 may include an inlet port 302 in fluid communication with the fluid reservoir 322. The outlet portion 302 may be coupleable to a return line for returning fluid from within the patient. In some aspects, the fluid reservoir 322 may contain a collapsible bag in fluid communication with the fluid channel 314 and the outlet port 308 so that fluid pressure forces experienced by the system are reduced or minimized. In some aspects, the cartridge 228 may not have a fluid reservoir 322 contained in the cartridge; it may simply have a fluid channel coupled to an external reservoir, such as shown in FIG. 1.

FIG. 13C shows a cross sectional view of the cartridge 228 of FIGS. 13A and 13B taken along lines 13C-13C. The cartridge 228 includes a first plate 241 and a second plate 243 attached to each other. The first plate 243 includes a thermally conductive surface 298 positioned adjacent a fluid reservoir 322 and a fluid channel 314. The second plate 243 includes the fluid reservoir 322 positioned at an upper portion 376 of the cartridge 228 and the fluid channel 314 in fluid communication with the fluid reservoir 322. The cartridge 228 may include a plurality of cavities 372 defined by a plurality of cross members 375 (FIG. 13A). The cavities 372 are sized and formed along the front portion cartridge to reduce the average thickness of the second plate, which consequently will improve heat transfer from the fluid in the cartridge 228 during operation of the cooling system. The cartridge 228 includes an upper angular surface 368 and a lower angular surface 374. The cartridge 228 has a profile to allow insertion of the cartridge 228 into the slot 358 of the front plate 234 for biasing to the cooling machine 236, as further discussed above.

The first plate 241 may have a thickness T to maintain a flat surface between the cartridge 228 and the thermal plate 238. If the first plate 241 is too thin for a specified metal, when place under vacuum, the first plate 241 may exhibit a rippled surface at locations along which the fluid channel 314 is positioned. This may create air pockets between thermally conductive surface 251 and the thermal plate 238, which thereby results in poor heat transfer from the fluid. In some embodiments, the thickness T of the first plate 241 is between 0.005 inch and 0.01 inch, but the thickness T may vary beyond such range. Preferably, the thickness T it is 0.01 inch.

As discussed above with reference to FIGS. 1-5A, the heat exchanger cartridge discussed with reference to FIGS. 8-13C could instead be a resilient body, such as a bag, removably coupled to the cooling device with a given biasing force for effectuating heat transfer from fluid contained in or traveling through the bag. The bag may include the same or similar features as the cartridges discussed in the present disclosure. For example, the bag may have a fluid channel having a serpentine pattern. The bag may have an outlet port in fluid communication with a treatment device positioned in a patient. At least one biasing mechanism may be coupled to the cooling device configured to bias the bag with a given force to chill the fluid to a selected temperature for delivery of a patient, such as further described elsewhere in the present disclosure. The at least on biasing mechanism may be the cam system 237 described above. Accordingly, a bag having a fluid chamber for holding a fluid may be inserted into a slot and a biasing member, such as a plate, may be actuated by the cam system to bias the biasing member against the bag, thereby biasing the bag against the cooling device with a given biasing force. Thus, the bag may be replaceable with a another bag by disengaging the cam system and the biasing plate from the bag to allow removal of the bag, similar or the same as described with reference to FIGS. 8-13C.

FIGS. 14-20 illustrate a system 410 that includes a fluid cooling supply system 412 coupled to a treatment system 417. The treatment system 410 shown in FIGS. 14-20 may have the same or similar features of the systems described and shown with reference to FIGS. 1-7B and 8-13C.

Figure 14:
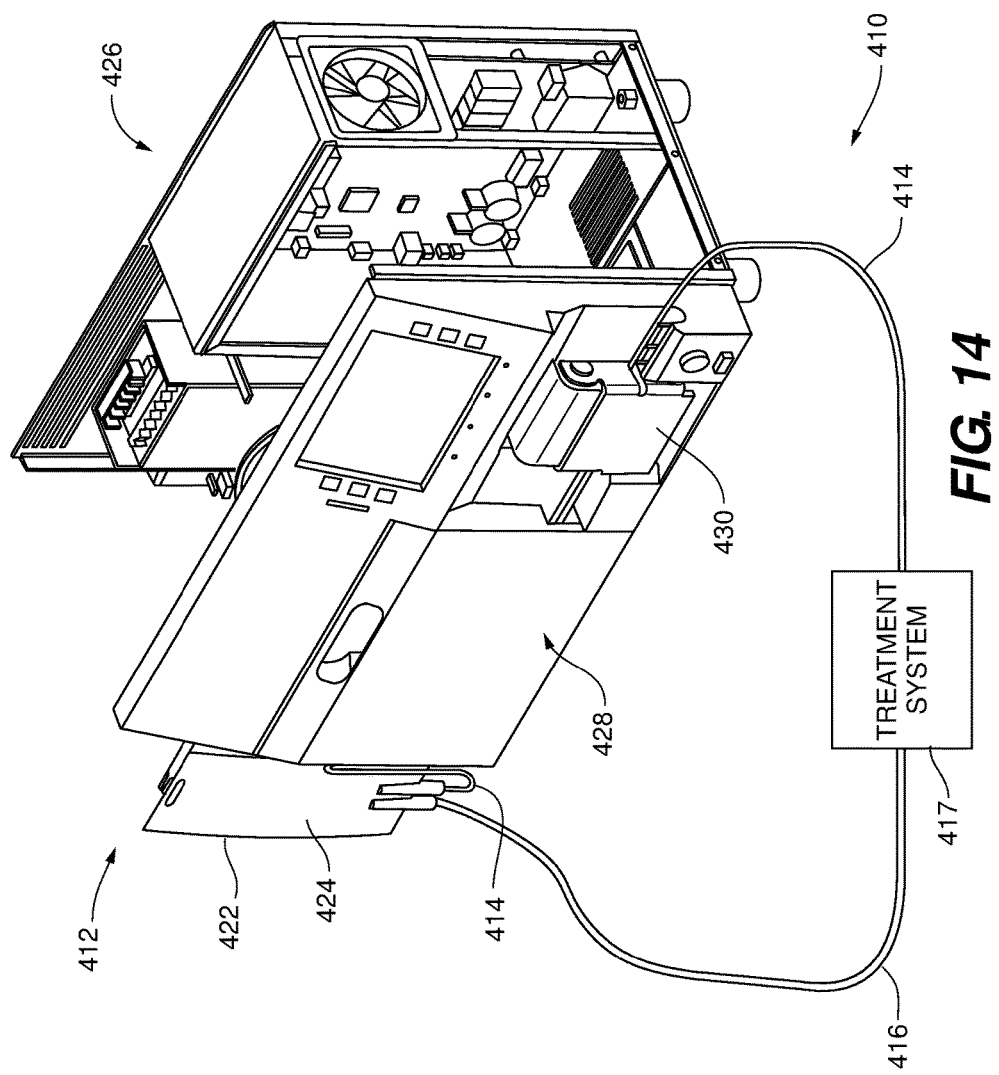
FIG. 14 is a perspective view of a treatment system having a fluid cooling delivery system according to one aspect.
Figure 15:
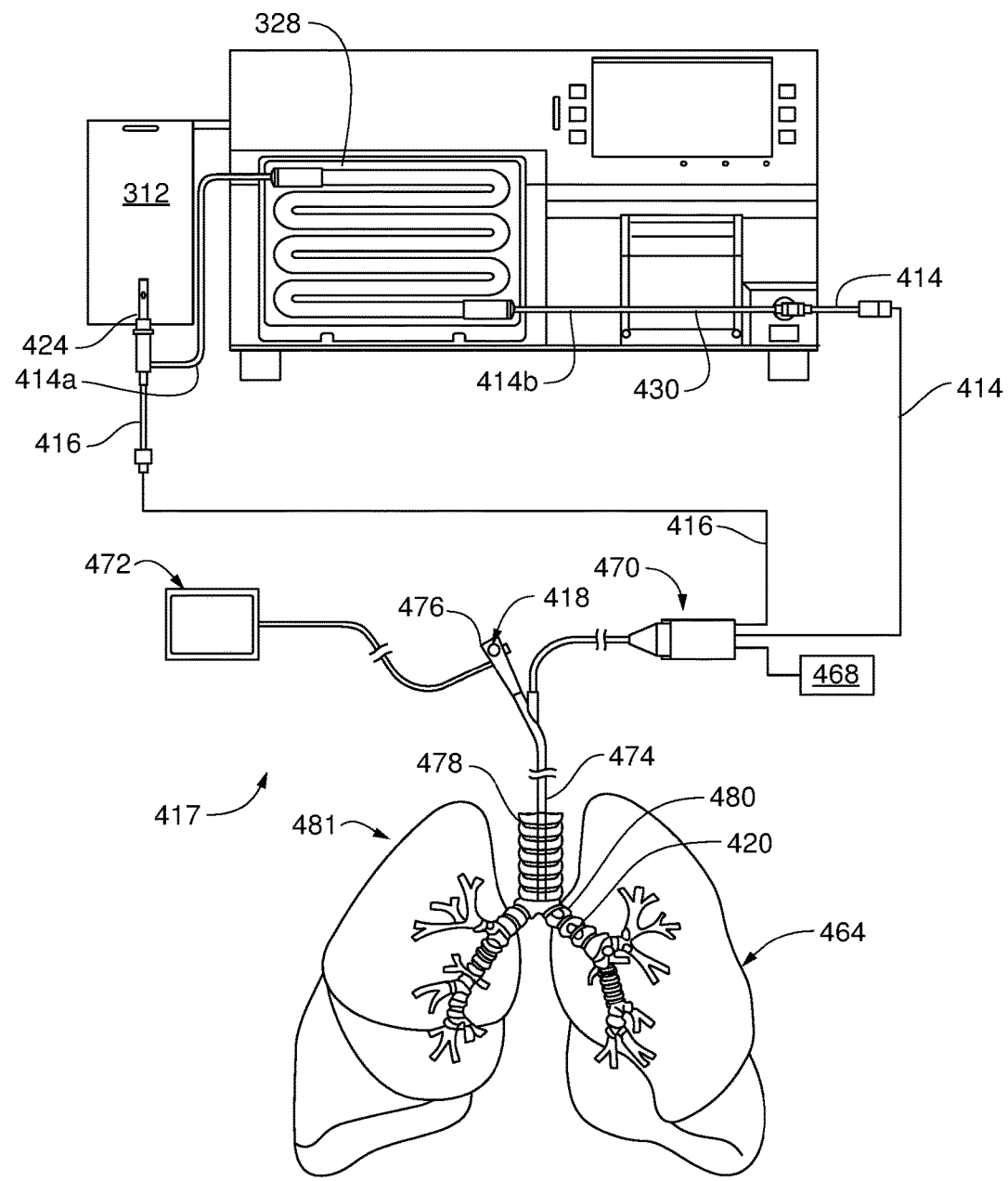
FIG. 15 is a front view of a fluid cooling delivery system and a schematic illustration of a treatment system during a treatment session according to one aspect.

In the example in FIG. 14, the fluid cooling supply system 412 is coupled to the treatment system 417. As described previously, the treatment system 417 may be positionable at least partially in a patient 464 (FIG. 15). The fluid cooling supply system 412 is configured to chill a fluid, pump a fluid, and supply the fluid through the treatment system 417. In a closed loop system, the fluid cooling supply system 412 may include a fluid reservoir 422, a fluid 424, a cooling system 426, a heat exchanger cartridge 428, a supply line 414 and a return line 416, which collectively cooperate to circulate cooled fluid through the treatment system 417 during treatment. The supply line 414 originates at the fluid reservoir 422 and extends through the cartridge 428 and along a pump 430. The supply line 414 may extend through a pulse damper (not depicted) for damping vibration of the supply line 414 during operation of the pump 430. Finally, the supply line 414 extends into the treatment system 417 positionable in a patient. The return line 416, in fluid communication with the supply line 414, originates at the treatment system 417 and extends from inside the patient and back to the reservoir 422 for recirculation of the fluid during treatment. In some embodiments, supply line 414 and return line 416 are connected to fluid reservoir 422 by a coaxial double spike 423 (FIGS. 15-16), which will be discussed in more detail below.

With reference to FIG. 15, and similar to the description of previous embodiments, in some aspects the pulmonary treatment system 417 may include a flexible bronchoscope 418 having a treatment device 420, a control portion 468, a steering mechanism 470, and a video system 472. The flexible bronchoscope 418 may include an insertion tube 474 extending from a control section 476 external to the patient's body, through the trachea 478, and to a treatment site within the left main bronchus 480 of the lungs 481 of a patient. The treatment device 420 can be positioned in the left main bronchus 480, or positioned in other locations, such as within the right main bronchi, the lobar bronchi, and bronchus intermedius. The treatment device 420 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. Based on the effectiveness of the treatment, the physician can concurrently or sequentially treat additional lobe(s).

The steering mechanism 470 may be coupled to the bronchoscope 418 and may receive the supply line 414 and the return line 416 to allow egress of the lines into the bronchoscope 418 and ultimately to the treatment device 420. The bronchoscope 418 may be coupled to the video system 472, which allows a practitioner to observe progress of the insertion tube 474 through the patient on a monitor 482 as the insertion tube 474 is steered with the assistance of the control portion 468. The video system 472 can also allow a practitioner to determine whether fluid is supplied to the treatment device 420 from the fluid cooling supply system 412. In addition, the bronchoscope 418 may be coupled to the control portion 468 to control some or all aspects of treatment, such as the amount of energy delivered to the treatment device 420. Accordingly, the treatment device 420 of the bronchoscope 418 is in fluid communication with the supply line 414 and the return line 416 of the fluid cooling supply system 412. As such, the fluid cooling supply system 412 is adapted to cool a fluid, pump the fluid, and circulate the fluid through the treatment device 420.

Figure 16:
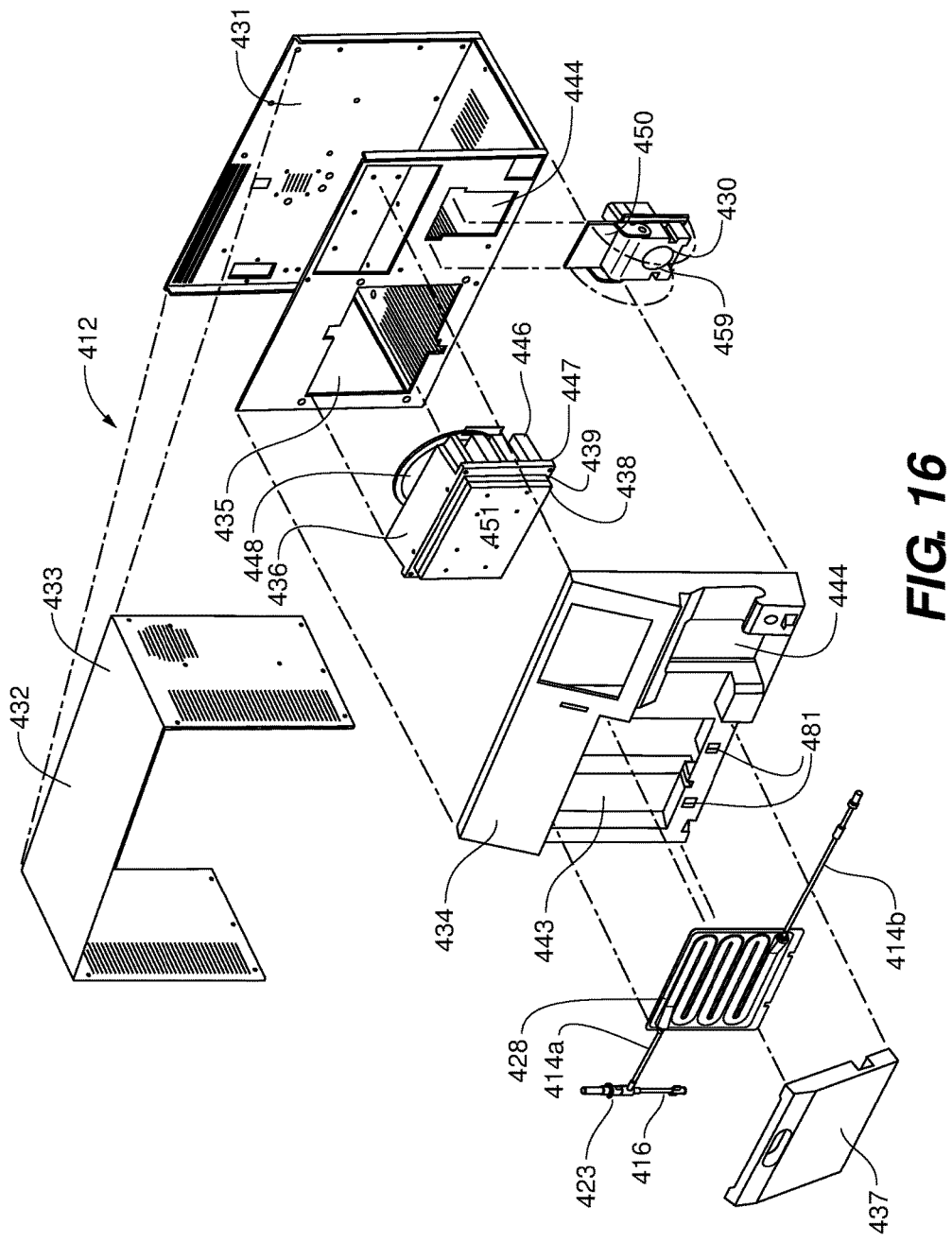
FIG. 16 is a partially exploded view of a fluid cooling delivery system according to one aspect.

With reference to FIG. 16, which shows a partially exploded view of certain components of the fluid cooling supply system 412 of FIGS. 14-15, and similar to the description of previous embodiments, in some aspects the fluid cooling supply system 412 may include: a housing 432 having a front plate 434; a cooling device 436 having a thermal plate 438 extending through the front plate 434; a pump 430 for pumping fluid; a heat exchanger cartridge 428 removably coupled to the front plate 434 and biased to and into contact with the cooling device 436; a hinged door 437 hingedly coupled to the front plate 434 of housing 423 for biasing the cartridge 428 to the thermal plate 438; and a controller 442 (FIG. 18) coupled to the pump 430 and cooling device 436.

The housing 432 may include a first portion 431 and second portion 433 secured to each other and to structurally support and house various components of the system. The first portion 431 may include an opening 435 for receiving and supporting a front portion of the cooling device 436. The cooling device 436 includes the thermal plate 438, a hot plate 439, fins 446, and a fan 448, as with commonly available TECs. The thermal plate 438 may include a planar surface 451 for biasing to the cartridge 428. The cooling device 436 may include a support plate 447 secured to the first portion 431 of the housing 432.

The front plate 434 may include an opening 444 for receiving a portion of the pump 430. The pump 430 may include a cover 450 and a rotating device 459 for coupling to the supply line 414. Pump 430 is positioned downstream of the cartridge 428 such that the fluid in the cartridge 428 experiences a negative fluid pressure and such that the fluid supplied to the treatment device 420 experiences a positive fluid pressure during normal operation of the treatment system.

With continued reference to FIG. 16, the front plate 434 may be attached to the front portion 431 of the housing 432. The front plate 434 and the housing 432 cooperate to structurally support the cooling device 436 and the pump 430. The front plate 434 includes an opening 443 for receiving the thermal plate 438 of the cooling device 436. In some embodiments, hinged door 437 pivots relative to the front plate 434 between an open position and a closed position. In the open position, cartridge 428 can be inserted into or removed from opening 443. In the closed position, cartridge 428 is biased against the thermal plate 438 of the cooling device 436.

Figure 17:
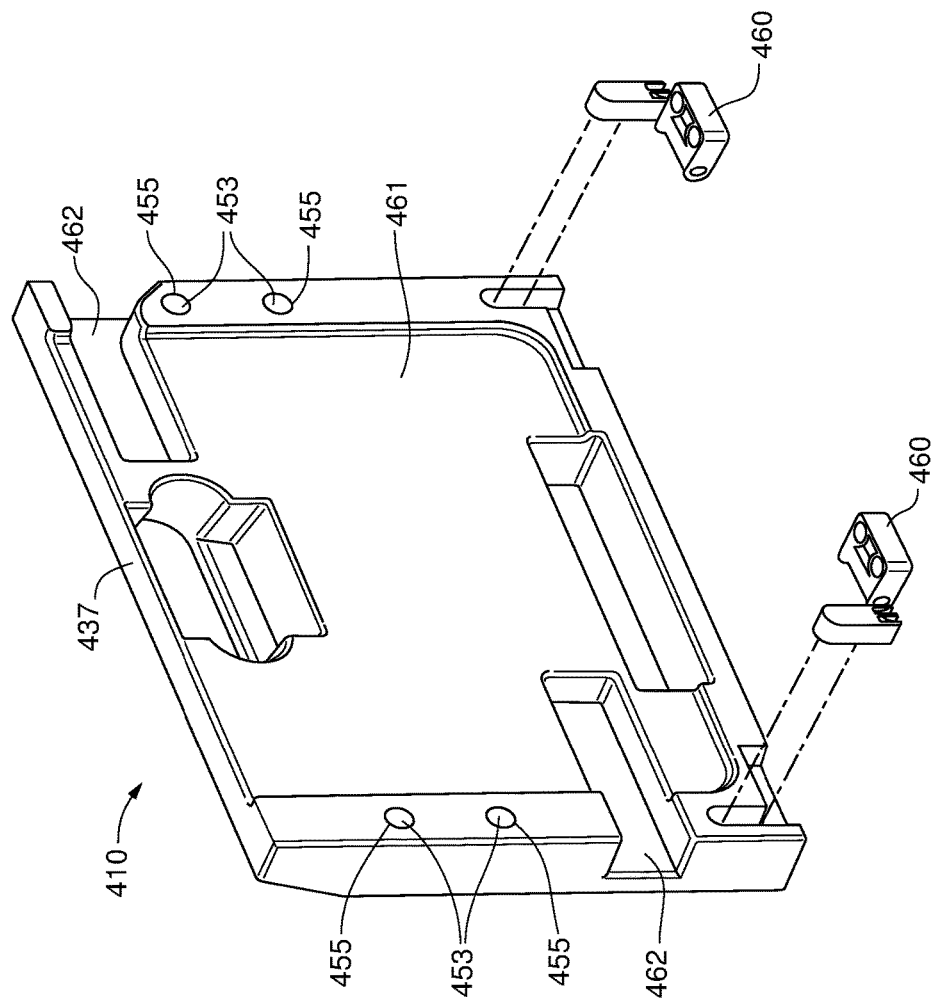
FIG. 17 is back perspective view of a hinged door assembly according to one aspect.

FIG. 17 shows back perspective view of a hinged door assembly 440 according to one aspect of the present disclosure. In some embodiments, the hinged door 437 can have at least one biasing mechanism that may include a plurality of magnets 453 (FIG. 17) for securing the hinged door 437 in the closed position. The magnets 453 may be secured into bores 455 defined in hinged door 437. Alternatively, one long magnet or a plurality of magnets can be secured along various portions of hinged door 437 or front plate 434 to achieve the same biasing force as discussed in the present disclosure. The biasing force provides improved surface-to-surface contact between the heat exchanger cartridge 428 and the thermal plate 438 of the cooling device 436, thereby improving and maintaining consistent and efficient heat transfer from the fluid during treatments.

Hinged door assembly 440 can also include a plurality of hinges 460 to couple the hinged door 437 to the front plate 434 or first portion 431 of housing 432. In one embodiment, the hinged door assembly 437 can include two hinges 460, thereby allowing hinged door 437 to pivotably shift relative to front plate 434 or first portion 431 of housing 432 between an open position and a closed position.

In one embodiment, hinged door 437 can be defined by a cutout 461 sized to receive and house a portion of heat exchanger cartridge 428. In one embodiment, hinged door 437 can include one or more cutouts 462 sized to receive and house the inlet port 402 and outlet port 408 and associated bubble traps of heat exchanger cartridge 428.

Figure 18:
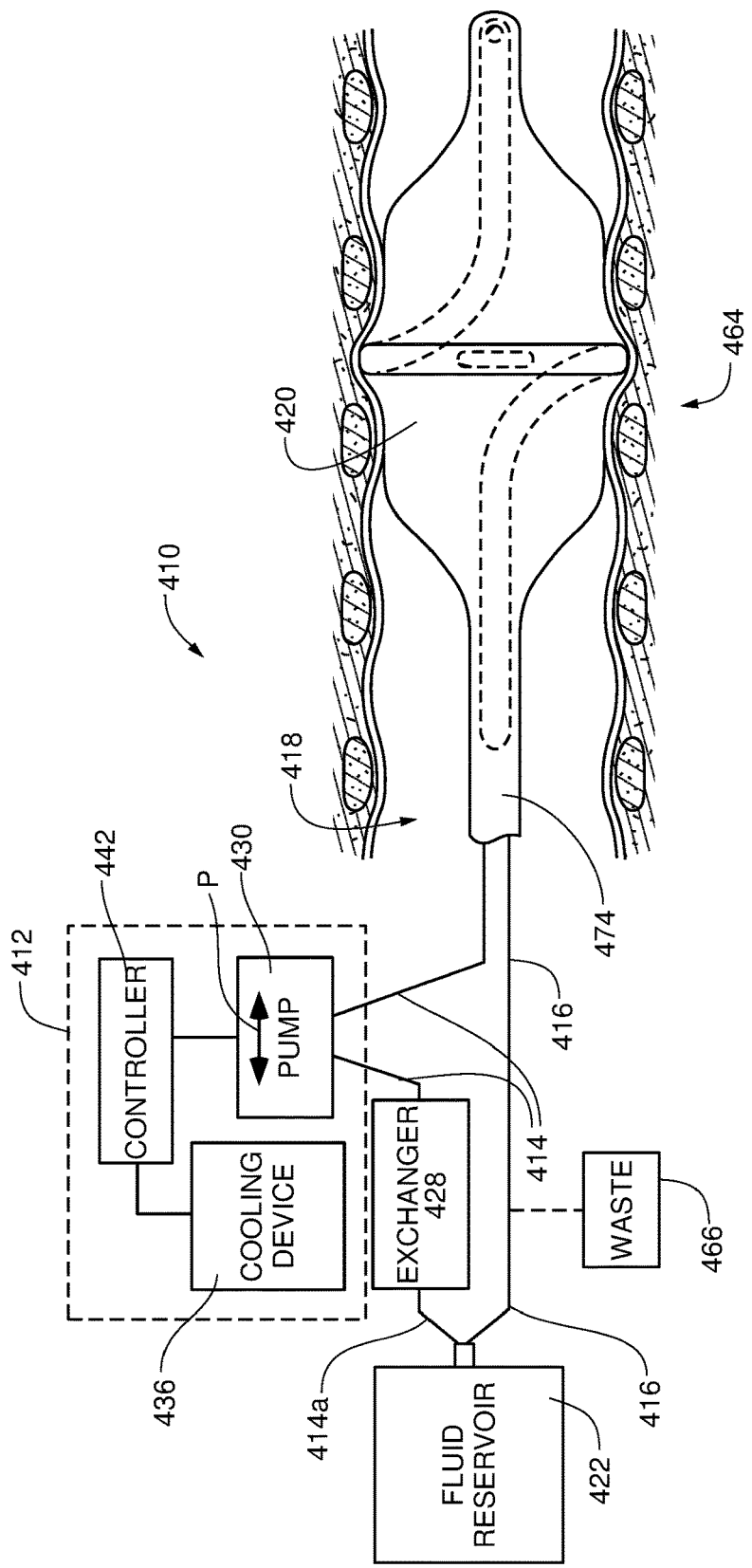
FIG. 18 is a schematic illustration of a fluid cooling delivery system coupled to an energy delivery device positioned in a patient during a treatment session according to one aspect.

FIG. 18 shows a schematic of a treatment system 410 in accordance with one embodiment of the invention, and similar to the schematic of treatment system 310 of FIG. 5. The treatment system 410 includes a fluid cooling supply system 412 coupled to a treatment device 420 positioned in a patient 464. In an embodiment, and similar to FIG. 5, the treatment device 420 can include one or more electrodes 90 that are each operable to output ultrasound, microwave, electrical energy, and/or radiofrequency (RF) energy.

The fluid cooling supply system 412 includes a cooling device 436, a heat exchanger 428, a pump 430, and a controller 442. The controller 442 may be coupled to the cooling device 436 and the pump 430 to regulate temperature and fluid circulation. The heat exchanger 428 may be removably coupled to the cooling device 436. A fluid supply line 414 originates at a fluid reservoir 422. The fluid supply line 414 continues to the heat exchanger 428 and through the pump 430 and terminates at the treatment device 420 for supplying chilled fluid to the patient 464. A fluid return line 416 continues from the treatment device 420 and may return either to the fluid reservoir 422 for recirculation and/or to a waste reservoir 419. Accordingly, the fluid may be drawn from the reservoir 422 through the heat exchanger 428 at a negative pressure by the pump 430. The fluid is chilled by the cooling device 436 as it travels through the heat exchanger 428. The fluid is supplied to the treatment device 420 at a positive pressure by the pump 430. The fluid may then be circulated through the treatment device 420 and returned from the treatment device 420 to outside the patient 464.

A control portion 468 (FIG. 15) can be coupled to the controller 442 for controlling aspects of the system. The controller 442 may be coupled to the pump 430 for regulating the speed and direction of the pump 430, thereby regulating the direction of flow and volume of fluid circulating through the system. The controller 442 may also be coupled to the cooling device 436 to regulate the temperature of the fluid in the cartridge 428, thereby further regulating the temperature of the fluid circulating through the treatment device 420, and thereby regulating the temperature of patient tissue during treatment.

The pump 430 may include forward and reverse gears, as depicted by arrows P, to draw and push the fluid forward through the heat exchanger 428 during treatment. The forward gear draws fluid from the heat exchanger 428 during normal operation of the system 410. Conversely, the reverse gear may push the fluid in reverse through the heat exchanger 428 to expel gas that may exist in the system 410. The speed and direction of the pump 430 may be controlled by the controller 442.

In some aspects, the pump 430 is coupled to a controller for variable control over the speed of the pump in order to control the amount of fluid delivery to the treatment device. Thus, the size and apposition pressure of the treatment device may be controlled by the variable speed controller. Moreover, a non-contact pressure measurement device may be electrically coupled to the pump and positioned proximate the high pressure side of the fluid path to regulate system pressure, such as by varying the speed of the pump in response to the pressure measured by the non-contact pressure measurement device, for example.

Figure 19B:
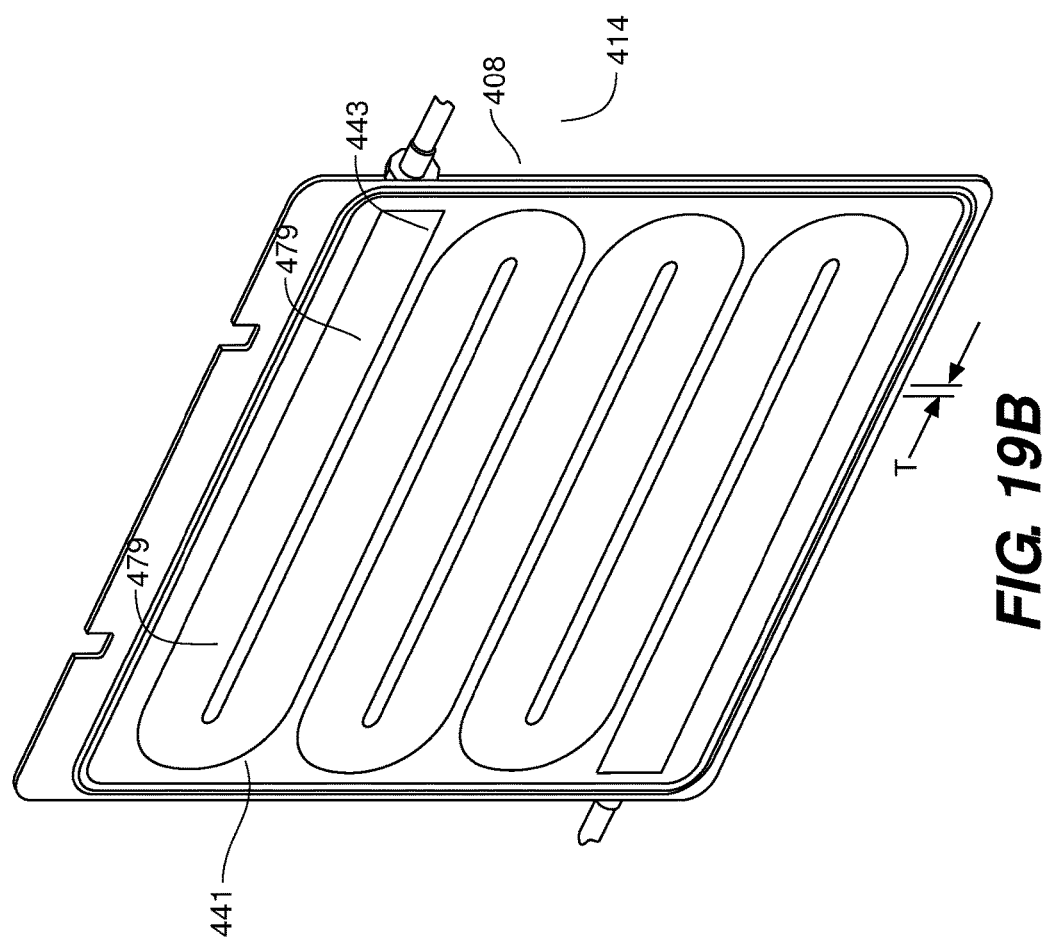
FIG. 19B is a back perspective view of a heat exchanger cartridge according to one aspect.

FIGS. 19A and 19B shows a front perspective view and a back perspective view, respectively, of a thermoformed heat exchanger cartridge 428 according to one aspect of the present disclosure. The heat exchanger cartridge 428 includes a flexible thermoformed tray 443 coupled or bonded to a first plate 441. The tray 443 coupled to the plate 441 defines a fluid channel 450 for fluidly coupling an inlet supply line 414a (uncooled fluid) and an outlet supply line 414b (cooled fluid) for introduction to the treatment device.

The first plate 441 is preferably comprised of a copper material and includes a thermally conductive surface 498 for biasing to the planar surface 451 of cooling device 436 (FIG. 16). For example, the first plate 441 can comprise a conductive material deposited on, such as by plating, coating (e.g. conductive inks or coatings), and/or laminating (e.g. thin films), a copper material to improve optimize thermal transfer between the fluid in the heat exchanger cartridge 428 and the cooling device 436. The conductive material can comprise silver, parylene, aluminum, or combinations thereof. The first plate 441 may have a thickness T to maintain a flat surface between the cartridge 428 and the thermal plate 438. If the first plate 441 is too thin for a specified metal, when placed under vacuum, such as when the pump is in reverse, the first plate 441 may exhibit a rippled surface at locations along which the fluid channel 450 is positioned. This may create air pockets between the first plate 441 and the thermal plate 438, which thereby results in poor contact, and therefore poor heat transfer from the fluid. It can also cause complete collapse of the recess of the tray thereby occluding the fluid channel. In some embodiments, the thickness T of the first plate 441 is between 0.005 inch and 0.015 inch, but the thickness T may vary beyond such range. Preferably, the thickness T is about 0.010 inch (or 10 mil).

In one particular embodiment, the plate 441 comprises a copper plate having a thickness of about 10 mil coated with a 0.5 to 1 micron of silver material. This provides a biocompatible and inert surface for the fluid to contact in the heat exchanger cartridge 428. Optionally, a parylene coating a provided over at least a portion of the silver material to provide barrier properties and to aid in sealing or bonding the tray 443 to the plate 441.

The thermoformed tray 443 is preferably comprised of transparent or translucent thermoformed material, such as polyvinyl chloride (PVC) or polyethylene terephthalate (PET). The material of the tray 443 exhibits sufficient flexibility such that it remains adhered to the plate 441 under high temperature applications such as sterilization. A thickness of the tray 443 is optimized to provide sufficient rigidity to the tray 443 such that when the system is pressurized in reverse, such that a vacuum is pulled, the tray does not deform and ripple so as not to compromise or significantly diminish heat exchanging characteristics of the cartridge 428. Optionally, an insulating foam or natural cork insulator (not shown) can be placed inside the cartridge 428 or on an outer surface of the cartridge 428 to thermally isolate the fluid from the ambient air temperature around the cartridge 428.

The tray 443 further includes a rim or recess 452 spaced inwardly from a perimeter of tray 443 by a sealing surface or flange 440. The sealing surface 440 may receive an adhesive, such as a UV activated or curable adhesive or an epoxy, to secure the plate 441 and tray 443 together. Any excess adhesive is collected into the recess 452 such that it does not interfere with fluid channel 450. Thus, the first plate 441 is secured to the tray 443 across various perimeter portions of the first plate 441, and prevents distortion of the copper plate due to suction forces or other forces acting on the first plate 441. In one embodiment, the first plate 441 and tray 443 are bonded using a UV curable adhesive and exposing the assembly to UV radiation. The transparency of the tray material allows for sufficient exposure to UV radiation to adequately cure the adhesive.

The fluid channel 450 is defined as the spaced between a recessed area formed in tray 443 and the first plate 441. The fluid channel acts to provide fluid communication between the fluid reservoir 422 and the pump 430 and ultimately the treatment device 420, while cooling the fluid passing through the fluid channel 450. In an embodiment, the fluid channel 450 serpentines throughout the cartridge 428 for a desired number of passes, such as seven passes as depicted. The number of passes as well as the depth and width of the channel 450 is selected based on a desired residence time of the fluid within the cartridge 428 to cool the fluid to a desired temperature. For example, the fluid reservoir 450 is dimensioned to provide adequate residence time for a coolant such as saline to be cooled from room temperature (25° C.) to about 0.1° C.-10° C., and more particularly to about 1° C. –6° C., and even more particularly, to about 3° C.-5° C., at a flow rate of about 100 mL/min.

Referring to FIG. 19A, an inlet port 402 is formed at a second end 450a of the fluid channel 450, and is in fluid communication with the inlet supply line 414a, which is in fluid communication with the fluid reservoir 422. An outlet port 408 is formed at a second end 450b of the fluid channel 450, is in fluid communication with the outlet supply line 414b. This portion of the supply line 414 is in fluid communication with the pump 430 and then through the bronchoscope 418 and to the treatment device 420 in the patient. In some aspects, the inlet port 402 and outlet port 408 can have a sloped profile with a starting depth greater than the depth of the fluid channel 450, sloping downward to a depth equal to the depth of the fluid channel. This allows for pooling of inlet fluid with a head space for the collection of gas bubbles in the system. In other words, any gas in the system tends to rise to the head space of ports 402 and 408.

The heat exchanger cartridge 428 has a profile to allow insertion of the cartridge 428 into a space between hinged door 437, and thermal plate 438 of cooling device 436. For example, in use, the cartridge 428 can be inserted into opening 443 when the hinged door 437 is open. When the hinged door 437 is closed, the cartridge 428 is biased against the thermal plate 438 of the cooling device 436, thereby sandwiching cartridge 428 between hinged door 437 and the thermal plate 438 of the cooling device 436 as further discussed above. In some embodiments, cartridge 428 can further be flanked by opening 443 defined in front plate 434. In some embodiments, heat exchanger cartridge 428 can include one or more notches 479 defined in one or more edges of the cartridge 428. The notches 479 can be sized to receive keys 481 of the front plate 434 for the purpose of ensure that cartridge 428 is inserted in an orientation that allows for normal operation.

Figure 20:
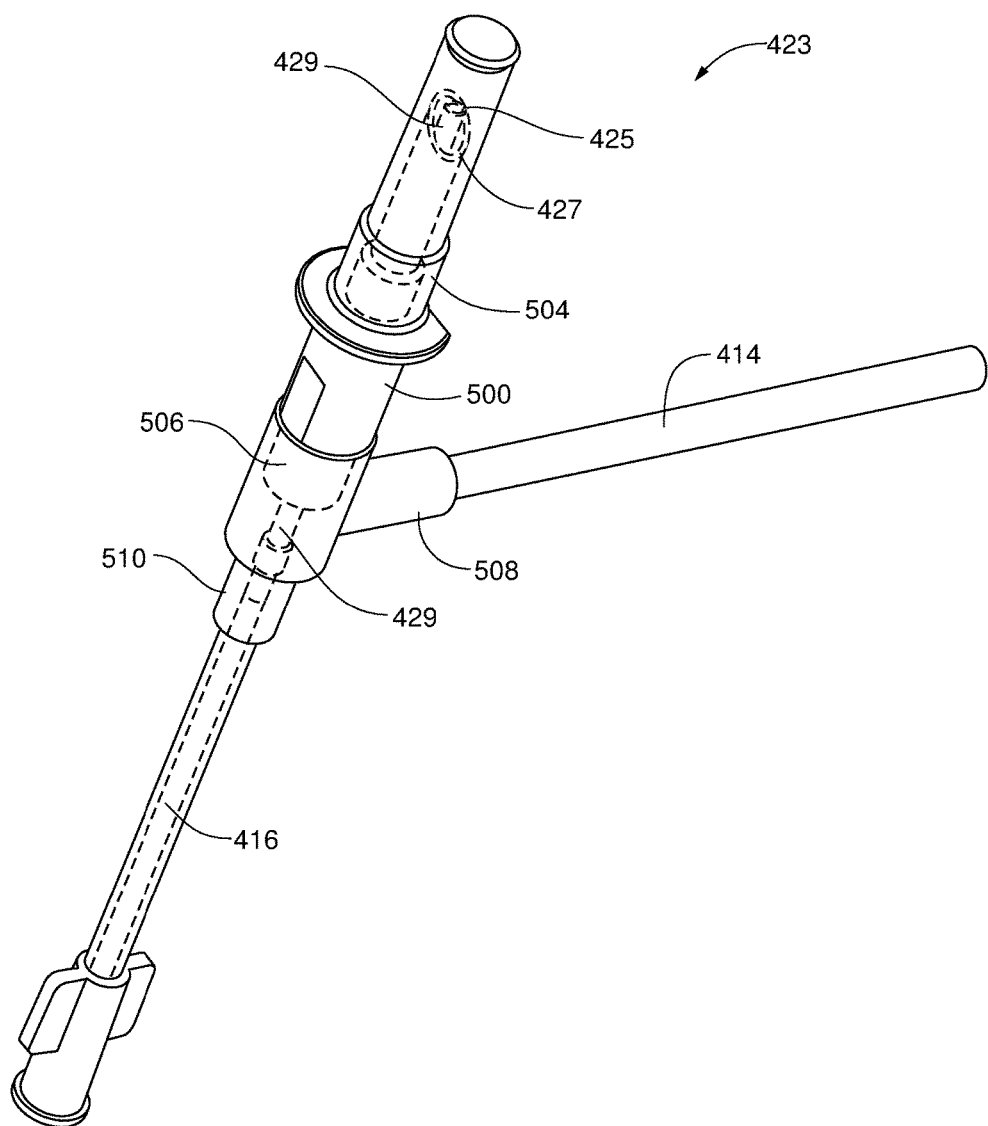
FIG. 20 is a back perspective view of a coaxial double spike assembly according to one aspect.

Referring now to FIG. 20, a perspective view of a coaxial bag spike assembly 423 for coupling the fluid reservoir 422 to the system 410 according to one aspect of the present disclosure is depicted. In some embodiments, supply line 414 and return line 416 can be connected to fluid reservoir 422 in a single location via the coaxial bag spike assembly 423 (see, for also, FIGS. 15-16). In this embodiment, return line 416 is in fluid connection with an inner channel 425, and supply line 414 is in fluid connection with an outer channel 427, coaxial with the inner channel 425. Both the inner and outer channels 425 and 427 are in fluid connection with the fluid reservoir 422 and the fluid 424 there within, but are isolated from each other. However, the reverse configuration can also be contemplated.

In one embodiment, the assembly 423 comprises a hypotube 429 having an internal diameter 431 inserted through a lumen of an injection molded non-vented spike female luer 500 having an internal diameter 502 greater than the internal diameter 431 of the hypotube 429 to create coaxial outer channel 427 and inner channel 425. The assembly 423 can further include a injection molded vented spike cap 504 coupled to a first end of the female luer 500, to fluidly connect the fluid reservoir 422 with the outer and inner channels 425. The assembly 423 also includes an injection molded bag spike adapter 506 having a first port 508 for coupling inlet supply line 414 to outer channel 427, and a second port 510 for coupling outlet supply line 316 to inner channel 425 of hypotube 429. The reverse configuration (i.e.

coupling inlet supply line 414 to the second port 510 and outlet supply line 416 to first port 508) can also be contemplated.

The internal diameter 431 of the hypotube is preferably sized to control back pressure in the treatment system 417, and or to effect pressure in an expandable member of the treatment device. Optionally, various clamps (not shown) can be used anywhere along the supply line 414 and/or return line 416 to further regulate supply and/or return flow of fluid to and from the reservoir 422. Accordingly, coaxial double spike 423 precludes the need for a separate supply and return spike by allowing fluid 424 to flow out of and into fluid reservoir simultaneously and at the same location on the reservoir 422.

The various embodiments and aspects described above can be combined to provide further embodiments and aspects. These and other changes can be made to the embodiments in light of the above-detailed description. The aspects, embodiments, features, systems, devices, materials, methods and techniques described herein may, in some embodiments, be similar to any one or more of the embodiments, features, systems, devices, materials, methods and techniques described in U.S. Pat. No. 8,088,127, PCT Application No. PCT/US2010/056424 filed Nov. 11, 2010 (Publication No. WO 2011/060200), U.S. application Ser. No. 12/913,702 filed on Oct. 27, 2010, U.S. application Ser. No. 12/944,666 filed Nov. 11, 2010, U.S. application Ser. No. 13/081,406 filed on Apr. 6, 2011, and U.S. Provisional Application No. 61/543,759. Each of these applications is incorporated herein by reference in its entirety. In addition, the aspects, embodiments, features, systems, devices, materials, methods and techniques described herein may, in certain embodiments, be applied to or used in connection with any one or more of the embodiments, features, systems, devices, materials, methods and techniques disclosed in the above-mentioned applications and patents.

Unless the context requires otherwise, throughout the specification and claims which follow, the word "comprise" and variations thereof, such as "comprises" and "comprising" are to be construed in an open, inclusive sense, that is, as "including but not limited to."

In general, in the following claims, the terms used should not be construed to limit the claims to the specific embodiments and aspects disclosed in the specification and the claims, but should be construed to include all possible embodiments and aspects along with the full scope of equivalents to which such claims are entitled. Accordingly, the claims are not limited by the disclosure.

The invention claimed is:

1. A system for treatment of a patient with a treatment device configured to be positioned in the patient, the system comprising:
   a treatment device;
   a cooling device that includes a thermal plate;
   a heat exchanger cartridge removably coupleable to the cooling device and the treatment device, the heat exchanger cartridge including:
      a thermally conductive surface,
      a plate coupled to the thermally conductive surface, the plate having structure defining a recessed area, the recessed area and thermally conductive surface thereby defining a fluid channel that extends through the heat exchanger cartridge, wherein the treatment device is fluidly coupleable to the heat exchanger cartridge at a first end of the fluid channel, and fluidly coupleable to the heat exchanger cartridge at a second end of the fluid channel, and a first port positioned proximate to and in fluid communication with the first end of the fluid channel, the first port being configured to connect to a fluid supply line of the treatment device along an axis which is parallel to and offset from the fluid channel at the first end; and
   a single pump positioned along the fluid supply line between the heat exchanger cartridge and the treatment device when the treatment device is fluidly coupled to the heat exchanger cartridge, wherein the single pump is configured to both draw a fluid through the fluid channel of the heat exchanger cartridge at a negative pressure to chill the fluid, and supply the chilled fluid to the treatment device at a positive pressure; and
   a fluid reservoir positioned between the treatment device and the heat exchanger cartridge when the treatment device is fluidly coupled to the heat exchanger cartridge, wherein the system is configured to deliver warmed fluid from the treatment device into the fluid reservoir and to deliver fluid from the fluid reservoir and through the heat exchanger cartridge to chill the fluid.

2. The system of claim 1, wherein the fluid cooling system further comprises at least one biasing mechanism arranged to removably couple the heat exchanger cartridge to the cooling device such that the thermally conductive surface is biased against the thermal plate of the cooling device to transfer heat from the fluid, the at least one biasing mechanism comprises two biasing mechanisms each positioned on opposing ends of the heat exchanger cartridge.

3. The system of claim 2, wherein the cooling device includes a perimeter portion having two corresponding biasing mechanisms, each being coupled to one of the two biasing mechanisms of the heat exchanger cartridge when the heat exchanger cartridge is engaged with the cooling device.

4. The system of claim 3, wherein the two biasing mechanisms and the two corresponding biasing mechanisms are magnets attractable to each other such that a given biasing force is applied between the heat exchanger cartridge and the cooling device to effectuate heat transfer from the fluid.

5. The system of claim 1, wherein the heat exchanger cartridge is formed to be in a first state when disengaged from the cooling device and in a second state when engaged to the cooling device, wherein the first state includes the thermally conductive surface of the cartridge having a first profile with a convex shape relative to the thermal plate, and wherein the second state includes the thermally conductive surface of the cartridge having a second profile that is a substantially flat shape relative to the thermal plate such that the thermally conductive surface of the cartridge and the thermal plate are substantially biased against each other to effectuate heat transfer from the fluid.

6. The system of claim 1, wherein the thermally conductive surface is substantially planar and has a thickness in a range of from about 0.005 inch to 0.015 inch.

7. The system of claim 1, wherein the plate is formed of a thermoformable material.

8. The system of claim 1, wherein the first port has a height which varies along a length of the first port such that the first port has a trapezoidal profile.

9. The system of claim 1, wherein the heat exchanger cartridge further comprises a second port positioned at and in fluid communication with the second end of the fluid channel for supplying fluid from the reservoir and to the treatment device, the second port being configured to connect to the fluid supply line of the treatment device along an axis which is parallel to and offset from the fluid channel at the second end.

10. The system of claim 1, further comprising a self-aligning means for automatic alignment of the heat exchanger cartridge to the thermal plate of the cooling device and automatic biasing of the heat exchanger cartridge to the thermal plate the cooling device.

11. The system of claim 1, further comprising at least one controller coupled to the cooling device for regulating an amount of heat transfer from the fluid.

12. The system of claim 1, wherein the pump is configured to circulate the fluid at a fluid flow rate of between 70 milliliters to 160 milliliters per minute.

13. The system of claim 1, wherein the pump is configured to deliver the fluid to the patient at a pressure between 25 psi and 150 psi.

14. The system of claim 1, further comprising a pump positioned downstream of the treatment device, the pump being configured to draw the fluid through the treatment device from the heat exchanger cartridge.

15. The system of claim 1, wherein at least a portion of the fluid supply line is configured to be positioned inside the patient and in fluid communication with the treatment device, the treatment device being configured to be positioned within a bronchus of the patient.

16. The system of claim 1, further comprising a bronchoscope, the treatment device being configured to be positioned adjacent to pulmonary tissue of the patient, and the heat exchanger being in fluid communication with the treatment device to supply chilled fluid to the patient during treatment.

17. The system of claim 1, wherein the system is a closed-loop system in which fluid is pumped from the fluid reservoir via the fluid supply line and back to the reservoir via a fluid return line after circulation through the treatment device.

18. The system of claim 17, wherein the fluid reservoir is in fluid communication with the fluid supply line and the fluid return line in a single location on the reservoir via a coaxial bag spike assembly.

19. The system of claim 18, wherein the coaxial bag spike assembly comprises a first tubular member having a first lumen therethrough and a first internal diameter, and a second tubular member having a second lumen therethrough and a second internal diameter smaller than the first diameter, wherein the second tubular member is positioned within the first lumen of the first tubular member, such that the first lumen and the second lumen are coaxial and thereby defining a first channel and a second channel.

20. The system of claim 19, wherein one of the first and second channels is in fluid communication with the fluid return line such that used fluid is returned to the reservoir via the channel, and wherein the other of the first and second channels is in fluid communication with the fluid supply line such that coolant is supplied from the reservoir to the fluid channel of the heat exchanger cartridge.

21. The system of claim 20, wherein each of the first and second lumens are coupled to the respective supply line and return line via a spike adapter, wherein the adapter comprises a tubular member coupled to a first end of the first tubular member, the adapter having a first port for coupling to the fluid return line such that the fluid return line and the one of the first and second channels are in fluid communication, and a second port for coupling to the fluid supply line such that the fluid supply line and the other of the first and second channels are in fluid communication.

22. The system of claim 19, wherein the second tubular member is a hypotube, and the first tubular member is a non-vented female luer.

23. A system for treatment of a patient with a treatment device configured to be positioned in the patient, the system comprising:
a treatment device;
a cooling device that includes a thermal plate;
a disposable heat exchanger cartridge removably couple-able to the cooling device and the treatment device, the cartridge including:
a thermally conductive surface, and
a plate coupled to the thermally conductive surface, the plate having structure defining a recessed area, the recessed area and thermally conductive surface thereby defining a fluid channel that extends through the heat exchanger cartridge, wherein the treatment device is fluidly coupleable to the heat exchanger cartridge at a first end of the fluid channel, and fluidly coupleable to the heat exchanger cartridge at a second end of the fluid channel;
at least one biasing mechanism arranged to removably couple the cartridge to the cooling device such that the thermally conductive surface is biased against the thermal plate of the cooling device to transfer heat from a fluid
a single pump positioned between the heat exchanger cartridge and the treatment device when the treatment device is fluidly coupled to the heat exchanger cartridge, wherein the single pump is configured to both draw the fluid through the fluid channel of the heat exchanger cartridge at a negative pressure to chill the fluid, and supply the chilled fluid to the treatment device at a positive pressure; and
a fluid reservoir positioned in a return path between the treatment device and the heat exchanger cartridge when the treatment device is fluidly coupled to the heat exchanger cartridge, wherein the system is configured to deliver warmed fluid from the treatment device into the fluid reservoir and to deliver fluid from the fluid reservoir and through the heat exchanger cartridge to chill the fluid,
wherein the fluid channel is dimensioned to provide a residence time sufficient for the fluid to undergo a temperature differential of about 15-35° C. at a flow rate of about 100 mL/minute therethrough when the thermally conductive surface is biased against the thermal plate.

24. The system of claim 23, wherein the at least one biasing mechanism includes a cam system operable between a first position for engaging the cartridge to the cooling device and a second position for disengaging the cartridge from the cooling device.

25. The system of claim 24, wherein the cam system includes a cam lever and a cam shaft having at least one cam lobe.

26. The system of claim 24, wherein the first position of the cam system is a locked configuration such that the thermally conductive surface of the cartridge is biased to the thermal plate to effectuate heat transfer, and wherein the second position is an unlocked configuration such that the cartridge can be removed from the cooling device.

27. The system of claim 23, further comprising a front plate coupled to the cooling device, the front plate having a slot sized to slideably receive the cartridge.

28. The system of claim 27, wherein the front plate includes an upper biasing surface and a lower biasing surface, the upper and lower biasing surfaces each being non-parallel to the thermal plate, and wherein the cartridge includes a corresponding upper angled surface and a corresponding lower angled surface, the corresponding upper and lower angled surfaces each being non-parallel to the thermal plate and each being respectively parallel to the upper and lower biasing surfaces of the front plate, such that the cartridge is slideably received in the slot.

29. The system of claim 28, wherein the at least one biasing mechanism includes a cam system operable between a first position for engaging the cartridge to the cooling device and a second position for disengaging the cartridge from the cooling device, wherein the first position includes the cam system biasing the upper biasing surface of the front plate such that the thermally conductive surface and the thermal plate are biased to each other at a given force.

30. The system of claim 23, wherein the plate is formed of a thermoformable material.

31. The system of claim 23, wherein the pump is configured to circulate the fluid at a fluid flow rate of between 70 milliliters to 160 milliliters per minute.

32. The system of claim 23, wherein the pump is configured to deliver the fluid at a pressure between 25 psi and 150 psi.

33. The system of claim 23, further comprising a pump positioned downstream of the treatment device, the pump being configured to draw the fluid through the treatment device.

34. The system of claim 23, further comprising a supply line in fluid communication with the fluid channel, wherein at least a portion of the supply line is configured to be positioned inside the patient and in fluid communication with the treatment device.

35. The system of claim 23, further comprising a bronchoscope, the treatment device being configured to be positioned adjacent to pulmonary tissue of the patient, and the cartridge being in fluid communication with the treatment device to supply chilled fluid to the patient during treatment.

* * * * *